(12) United States Patent
Sugiyama

(10) Patent No.: US 8,956,869 B2
(45) Date of Patent: Feb. 17, 2015

(54) PEPTIDE INHIBITING DIFFERENTIATION OF HEMATOPOIETIC STEM CELLS OR HEMATOPOIETIC PRECURSOR CELLS AND USE OF SAME

(75) Inventor: Daisuke Sugiyama, Fukuoka (JP)

(73) Assignee: Kyushu University, National University Corporation, Fukuoka (JP)

(*) Notice: Subject to any disclaimer, the term of this patent is extended or adjusted under 35 U.S.C. 154(b) by 3 days.

(21) Appl. No.: 13/499,116

(22) PCT Filed: Sep. 29, 2010

(86) PCT No.: PCT/JP2010/067011
§ 371 (c)(1),
(2), (4) Date: Mar. 29, 2012

(87) PCT Pub. No.: WO2011/040500
PCT Pub. Date: Apr. 7, 2011

(65) Prior Publication Data
US 2012/0315701 A1    Dec. 13, 2012

(30) Foreign Application Priority Data
Sep. 29, 2009 (JP) ................. 2009-224088

(51) Int. Cl.
| C12N 5/0789 | (2010.01) |
| C12N 5/071 | (2010.01) |
| C07K 16/18 | (2006.01) |
| C07K 7/06 | (2006.01) |
| C07K 7/08 | (2006.01) |
| C07K 16/28 | (2006.01) |

(52) U.S. Cl.
CPC ............. *C12N 5/0647* (2013.01); *C07K 7/06* (2013.01); *C07K 7/08* (2013.01); *C07K 16/28* (2013.01); *C12N 2501/125* (2013.01); *C12N 2501/14* (2013.01); *C12N 2501/145* (2013.01); *C12N 2501/2303* (2013.01); *C12N 2501/2306* (2013.01); *C12N 2501/998* (2013.01); *C12N 2502/02* (2013.01)
USPC ........ 435/377; 530/327; 530/328; 530/387.9; 435/325

(58) Field of Classification Search
CPC ..... A61K 38/556; A61K 35/34; A61K 38/39; A61K 38/00; A61K 38/179; A61K 38/18; A61K 8/64; A61L 2300/414; A61L 27/3834; C12N 5/0647; C12N 5/0662; C12N 5/0663; C12N 5/0665
See application file for complete search history.

(56) References Cited

U.S. PATENT DOCUMENTS

| 6,613,565 B1 * | 9/2003 | Witte et al. ............. 435/372 |
| 7,745,391 B2 * | 6/2010 | Mintz et al. ............. 514/19.3 |
| 2009/0299038 A1 | 12/2009 | Nakamura et al. |

FOREIGN PATENT DOCUMENTS

| JP | H08-509358 A | 10/1996 |
| JP | 2000-513329 A | 10/2000 |
| JP | 2007-106760 | 4/2007 |
| JP | 2007-238473 | 9/2007 |
| WO | 94/13701 A2 | 6/1994 |
| WO | 97/31647 A1 | 9/1997 |
| WO | 00/11168 A2 | 3/2000 |
| WO | 2009/116670 A1 | 9/2009 |

OTHER PUBLICATIONS

Deiuliis et al. Alternative splicing of delta-like 1 homolog (DLK1) in the pig and human. Comp Biochem Physiol B Biochem Mol Biol. 2006;145(1):50-59.*
Baladron et al. The EGF-like Homeotic Protein dlk Affects Cell Growth and Interacts with Growth-Modulating Molecules in the Yeast Two-Hybrid System. Biochem Biophys Res Commun. 2002; 291(2):193-204.*
Verano-Braga et al. *Tityus serrulatus* Hypotensins: A new family of peptides from scorpion venom. Biochem Biophys Res Commun. Jul. 4, 2008;371(3):515-20.*
Ingrid Fleming. Signaling by the Angiotensin-Converting Enzyme. Circulation Research. 2006; 98: 887-896.*
Jokubaitis et al. Angiotensin-converting enzyme (CD143) marks hematopoietic stem cells in human embryonic, fetal, and adult hematopoietic tissues. Blood. 2008 111: 4055-4063.*
Li et al. The Human Homolog of Rat Jagged1 Expressed by Marrow Stroma Inhibits Differentiation of 32D Cells through Interaction with Notch1. Immunity. Jan. 1998;8(1):43-55.*
Ncbi search SEQ ID No. 1-10.*
Smas C.M., et al.; "Pref-1, a Protein Containing EGF-like Repeats, Inhibits Adipocyte Differentiation," Cell; May 21, 1993; vol. 73; No. 4; p. 725-734 (Cited in the International Search Report).
(Continued)

*Primary Examiner* — Karlheinz R Skowronek
*Assistant Examiner* — Jia-Hai Lee
(74) *Attorney, Agent, or Firm* — Kratz, Quintos & Hanson, LLP

(57) ABSTRACT

The present invention provides a novel peptide that can be effectively used to produce or grow tissue-specific stem cells or tissue-specific progenitor cells in vitro. The peptide of the invention is a peptide having an amino acid sequence consisting of the amino acid residues set forth in SEQ ID NO:1, or an analog thereof. A feature of the peptide of the invention is having at least one of the following effects: (1) an effect of inhibiting differentiation of hematopoietic stem cells or hematopoietic progenitor cells into myeloid cells, (2) an effect of promoting amplification of mesenchymal stem cells, and (3) an effect of inducing hematopoietic stem cells from pluripotent stem cells.

5 Claims, 20 Drawing Sheets

(56) References Cited

OTHER PUBLICATIONS

International Search Report issued for a counterpart International Application No. PCT/JP2010/067011, dated Oct. 26, 2010.
Li, Liang, et al., "Expression of DLK/PREF1 Results in Inhibition of Human Myeloid Cell Differentiation and Proliferation through Distinct Molecular Mechanisms" Blood, vol. 104 (2004), Abstract (p. 62A).
Nov. 12, 2009, "Human delta-like 1 homolog (DLK1) protein fragment (residues 92 to 167).", XP002693973, retrieved from EBI accession No. GSP:AXQ82752 Database accession No. AXQ82752.
Mar. 18, 2008, "SubName: Full=Delta-like 1; Flags: Fragment;", XP002693974, retrieved from EBI accession No. UNIPROT:B0LAC1, Database accession No. B0LAC1.
Nov. 1, 1995, "RecName: Full=Protein delta homolog 1; Short=DLK-1; AltName: Full=Adipocyte differentiation inhibitor protein; AltName: Full=Preadipocyte factor 1; Short=Pref-1, Contains: RecName: Full=Fetal antigen 1;", XP002693975, retrieved from EBI accession No. UNIPROT: Q09163 Database accession No. Q09163.
Oct. 3, 2006, "SubName: Full=Delta-like 1 isoform C2;", XP002693976, retrieved from EBI accession No. UNIPROT:Q0H2C8 Database accession No. Q0H2C8.
Ruddock, Nancy T., et al., "Analysis of Imprinted Messenger RNA Expression During Bovine Preimplantation Development," Biology of Reproduction, vol. 70 (2004), pp. 1131-1135.
Fahrenkrug, Scott C., et al., "Genomic Organization and Genetic Mapping of the Bovine PREF-1 Gene," Biochemical and Biophysical Research Communications, vol. 264 (1999), pp. 662-667.
Edwards, Carol A., et al., "The Evolution of the *DLK1-DIO3* Imprinted Domain in Mammals," PLOS Biology, vol. 6, Issue 6 (2008), pp. 1292-1305.
Oct. 14, 2008, "SubName: Full=Delta-like 1;" XP002693977, retrieved from EBI accession No. UNIPROT: B5LY06 Database accession No. B5LY06.
Oct. 14, 2008, "SubName: Full=Delta-like 1;" XP002693978, retrieved from EBI accession No. UNIPROT: B5LY07 Database accession No. B5LY07.
Abdallah, Basem M., et al., "Regulation of Human Skeletal Stem Cells Differentiation by Dlk 1/Pref-1," Journal of Bone and Mineral Research, vol. 19, No. 5 (2004), pp. 841-852.
Sakajiri, S., et al., "Dlk1 in normal and abnormal hematopoiesis," Leukemia, vol. 19 (2005), pp. 1404-1410.
Kiuth, Simone Maria, et al., "DLK-1 as a Marker to Distinguish Unrestricted Somatic Stem Cells and Mesenchymal Stromal Cells in Cord Blood," Stem Cells and Development, vol. 19, No. 10 (2010), pp. 1471-1483.
Supplementary European Search Report dated Apr. 15, 2013, in the corresponding European patent application No. 10820615.2.

* cited by examiner

Green : c-Kit (HEMATOPOIETIC STEM CELL)
Red : DLK-1 (HEPATOBLAST)
Blue : TOTO-3 (NUCLEUS)

(A)

(B)

KS-13 (−)          KS-13 (+)
                   30 μg/mL

Green : c-Kit (HSC marker)
Red : KS-13 (A novel peptide)
Blue : TOTO-3 (Nucleus)

(A)

(B)

PEPTIDE INHIBITING DIFFERENTIATION OF HEMATOPOIETIC STEM CELLS OR HEMATOPOIETIC PRECURSOR CELLS AND USE OF SAME

TECHNICAL FIELD

The present invention relates to a novel peptide that can be effectively used to produce or grow tissue-specific stem cells or tissue-specific progenitor cells in vitro. More specifically, the present invention relates to a peptide that has at least one of the following effects: (1) an effect of inhibiting differentiation of hematopoietic stem cells or hematopoietic progenitor cells, (2) an effect of promoting amplification of mesenchymal stem cells, and (3) an effect of inducing hematopoietic stem cells from pluripotent stem cells.

The present invention further relates to use of the peptide, and more specifically to use of the peptide as a reagent (or a pharmaceutical preparation) for in vitro production or growth of tissue-specific stem cells or tissue-specific progenitor cells. More specifically, the present invention relates to use of the peptide as a hematopoietic stem cell or hematopoietic progenitor cell differentiation inhibitor, use of the peptide as a mesenchymal stem cell amplification promoter, and use of the peptide as a hematopoietic stem cell inducer. As another use of the peptide, the present invention further relates to a method for in vitro growth of tissue-specific stem cells or tissue-specific progenitor cells using the peptide, and to a method for in vitro induction or production of hematopoietic stem cells using the peptide.

The present invention further relates to an antibody to the peptide.

BACKGROUND ART

If it is possible to produce hematopoietic stem cells from pluripotent stem cells in vitro, or remove hematopoietic stem cells from the living body, and culture and amplify only hematopoietic stem cells while preventing neoplastic transformation, it will solve many transplant-related problems and expand applications of hematopoietic stem cell transplantation therapy, as well as enabling exploration of new tissue engineering, such as development of other organ-specific stem cell transplantation therapy. The following problems have been pointed out regarding hematopoietic stem cell production and amplification methods developed up to now:

1. Introduction of HoxB4 gene into pluripotent stem cells can produce hematopoietic stem cells, but also induces acute leukemia.
2. Introduction of HoxB4 gene into hematopoietic stem cells amplifies hematopoietic stem cells, but also induces acute leukemia.
3. Addition of cytokine induces differentiation of mature blood cells. As a result, it becomes difficult to maintain the undifferentiated state of hematopoietic stem cells.
4. Addition of a demethylating agent increases amplification efficiency of hematopoietic stem cells, but also affects epigenetics. Therefore, safety must be checked.

Theoretically, pluripotent stem cells can be differentiated into any cell lineage. However, no technique of determining the direction of cell differentiation in vitro has been established yet. Furthermore, no technique of preparing clinically applicable cells from hematopoietic stem cells has been established. Pluripotent stem cells have a property that once the cells differentiate into a lineage, the cells lose the ability to differentiate into other lineages. If it is possible to inhibit pluripotent stem cells from differentiating into cells other than hematopoietic stem cells, production of hematopoietic stem cells from pluripotent stem cells can be expected. Hematopoietic stem cells have apparently incompatible abilities, i.e., self-renewal ability and pluripotency. Differentiation of hematopoietic stem cells subjected to stimulation such as a cytokine produces mature blood cells. More specifically, to amplify hematopoietic stem cells, accelerating self-renewal while inhibiting differentiation into various cell lineages is necessary. To develop new hematopoietic stem cell production and amplification methods while overcoming the aforementioned problems, search for and development of the following factors are important: a factor that inhibits differentiation of cells other than hematopoietic stem cells, a factor that promotes only self-renewal of hematopoietic stem cells, and a factor that inhibits differentiation of hematopoietic stem cells. A fetal liver is a principal site for hematopoietic stem cell amplification in vivo. Accordingly, to search for and develop new factors, elucidation of the amplification mechanism of hematopoietic stem cells in the liver and reproduction of the results in a test tube, i.e., taking a orthodox approach, will be a quick way.

Patent Literature (PTL) 1 discloses a hematopoietic stem cell proliferator comprising a placenta-constituting cellular debris as an active ingredient. However, such a biologically derived material has problems, such as infection and difficulty in preparing the material.

Patent Literature (PTL) 2 discloses a factor for promoting the maintenance and amplification of hematopoietic stem cells, comprising a membrane protein Thsd1/Tmtsp. However, preparing such a membrane protein in an active form is difficult.

CITATION LIST

Patent Literature

PTL 1: Japanese Unexamined Patent Publication No. 2007-106760
PTL 2: Japanese Unexamined Patent Publication No. 2007-238473
PTL 3: WO97/31647
PTL 4: WO00/11168

SUMMARY OF INVENTION

Technical Problem

Hematopoietic stem cell transplantation therapy has been used for haematopoietic diseases and also used for a wide variety of other purposes such as autoimmune diseases, malignant solid tumors, and regenerative medicine. Autologous bone marrow, donor bone marrow, and umbilical cord blood are currently used as sources of hematopoietic stem cells for transplantation. However, the use of donor bone marrow or umbilical cord blood has the following problems: shortage of the absolute number of hematopoietic stem cells for transplantation, donor shortage, graft failure due to immune response, and graft-versus-host disease.

If hematopoietic stem cells can be produced from pluripotent stem cells in vitro, the obtained cells can be used as a new tool that does not depend on supply sources such as bone marrow, peripheral blood, and umbilical cord blood. Furthermore, in vitro production, cultivation, and amplification of hematopoietic stem cells would provide a sufficient amount of the stem cells for transplantation therapy at any time by simply collecting a small amount of the stem cells from the patient's own bone marrow, etc. Without the necessity of waiting for an HLA-matched donor, safe transplantation can be performed. That is, in addition to ensuring availability of the stem cells in number necessary for transplantation, autologous transplantation that does not cause rejection can be preformed. Even when autologous transplantation is impossible, if an amplification technique is established, transplantation therapy can be performed by collecting only a small amount of cells from the donor's bone marrow. This will reduce the donor's risk and increase the number of donors enrolled for bone marrow banks, thus increasing the chances of finding a donor. If umbilical cord blood can also be amplified in vitro, the obtained product can be used to treat adults. Thus, establishment of the techniques for in vitro production and amplification of hematopoietic stem cells can save the lives of many patients with intractable blood disorders. Furthermore, stem cells necessary for gene therapy become easily available, which enables safe gene transfer not using a retrovirus, and gene therapy is expected to become more common. The development of techniques for producing and amplifying hematopoietic stem cells in vitro is a significant pressing technological challenge to be solved for regenerative therapy and gene therapy as well as for transplantation therapy for intractable blood disorder patients.

In view of the above, an object of the present invention is to provide a novel peptide that is effectively usable as one of the following factors in the in vitro production or growth of tissue-specific stem cells or tissue-specific progenitor cells of a vertebrate, particularly mammals: (1) a factor that inhibits differentiation of hematopoietic stem cells or hematopoietic progenitor cells, (2) a factor that promotes amplification of mesenchymal stem cells, and (3) a factor that induces and produces hematopoietic stem cells from pluripotent stem cells. Another object of the present invention is to provide (i) use of the peptide as a hematopoietic stem cell or hematopoietic progenitor cell differentiation inhibitor, (ii) use of the peptide as a mesenchymal stem cell amplification promoter, and (iii) use of the peptide as a hematopoietic stem cell inducer. Another object of the present invention is to provide a method for in vitro induction or production of hematopoietic stem cells using the peptide, and a method for in vitro growth of tissue-specific stem cells or tissue-specific progenitor cells using the peptide.

Solution to Problem

The present inventor found that a peptide having an effect of inhibiting differential growth of hematopoietic stem cell is present among a plurality of peptides designed based on the extracellular domains of various membrane surface proteins expressed in hepatoblasts of a human fetal liver where hematopoietic stem cells are amplified. As a result of further research, the inventor confirmed that this peptide has an effect of inhibiting differentiation of hematopoietic stem cells or hematopoietic progenitor cells into myeloid cells in vitro, for example, in a test tube, and allowing autonomous growth (amplification) of non-myeloid pre-erythroid cells, as well as mixed hematopoietic progenitor cells that can differentiate into blood cells of multiple lineages. Thus, the inventor confirmed that this peptide is effective as a "hematopoietic stem cell or hematopoietic progenitor cell differentiation inhibitory factor". Further, the present inventor further found that this peptide also has an effect of promoting autonomous growth (amplification) of mesenchymal stem cells that are believed to have an ability to differentiate into osteoblasts, adipocytes, muscle cells, chondrocytes, and like mesenchymal cells. Thus, the inventor confirmed that this peptide is effective as a "mesenchymal stem cell amplification promoting factor." Further, the present inventor found that this peptide has an effect of specifically inducing hematopoietic stem cells from pluripotent stem cells, such as ES cells, and confirmed that this peptide is effective as a "hematopoietic stem cell inducer." These results suggest that by culturing tissue-specific stem cells, such as hematopoietic stem cells and mesenchymal stem cells, or tissue-specific progenitor cells in the presence of the peptide developed by the present inventor, these cells can be grown while differentiation thereof is inhibited. The results further suggest that by culturing pluripotent stem cells in the presence of the peptide developed by the present inventor, hematopoietic stem cells can be specifically induced and produced in vitro. That is, this peptide is a very promising material that can solve the source problem of hematopoietic stem cells for transplantation in hematopoietic stem cell transplantation therapy.

The present invention was accomplished based on these findings and includes the following embodiments.

(I) Novel Peptide (I-1) A peptide set forth in (A) or (B) below:

(A) a peptide consisting of 13 amino acid residues having an amino acid sequence set forth in SEQ ID NO: 1; and (B) a peptide comprising the amino acid sequence set forth in SEQ ID NO: 1, wherein one or more amino acid residues are deleted, substituted, or added, the peptide having at least one of the following effects:

(1) an effect of inhibiting differentiation of hematopoietic stem cells or hematopoietic progenitor cells into myeloid cells;

(2) an effect of promoting amplification of mesenchymal stem cells; and (3) an effect of inducing hematopoietic stem cells from pluripotent stem cells.

(I-2) The peptide according to (I-1), wherein the peptide set forth in (B) comprises an amino acid sequence consisting of amino acid residues shown below:

```
                                    (SEQ ID NO: 2)
{(Cys XXa XXb)_n XXc XXd}_m Gly Pro Cys XXe

XXf Asn Gly Ser
```

(wherein XXa is an amino acid residue of Gln or His; XXb is an amino acid of His, Lys, Glu, or Leu; XXc is an amino acid residue of Lys or Met; XXd is an amino acid of Ala, Asp, Glu, or Gln; XXe is an amino acid residue of Val, Ala, or Ile; and XXf is an amino acid residue of Ile, Met, or Val; and n and m independently represent an integer of 1 or 0; provided, however, that all the following conditions are not simultaneously met: XXa is Gln, XXb is Lys, XXc is Lys, XXd is Asp, XXe is Val, and XXf is Ile.)

(I-3) The peptide according to (I-1) or (I-2), wherein the peptide set forth in (B) comprises any one of the amino acid sequences consisting of amino acid residues shown below:

```
                                    (SEQ ID NO: 3)
Cys Gln His Lys Ala Gly Pro Cys Val Ile

Asn Gly Ser (SEQ ID NO: 4)
Cys Gln Lys Lys Asp Gly Pro Cys Val Met

Asn Gly Ser (SEQ ID NO: 5)
Cys Gln His Lys Ala Gly Pro Cys Val Ile

Asn Gly Ser
```

```
                                                    (SEQ ID NO: 6)
Cys Gln Glu Met Asp Gly Pro Cys Val Val

Asn Gly Ser (SEQ ID NO: 7)
Cys His Leu Lys Glu Gly Pro Cys Val Ile

Asn Gly Ser (SEQ ID NO: 8)
Lys Glu Gly Pro Cys Val Ile Asn Gly Ser (SEQ ID NO: 9)
Cys His Leu Lys Gln Gly Pro Cys Ile Ile

Asn Gly Ser (SEQ ID NO: 10)
Gly Pro Cys Ile Ile Asn Gly Ser.
```

(II) Hematopoietic Stem Cell or Hematopoietic Progenitor Cell Differentiation Inhibitor and Use Thereof (II-1) A hematopoietic stem cell or hematopoietic progenitor cell differentiation inhibitor comprising at least one of the peptides set forth in any one of (I-1) to (I-3) or a pharmaceutically acceptable salt or solvate thereof as an active ingredient.

(II-2) A method for inhibiting differentiation of hematopoietic stem cells or hematopoietic progenitor cells, comprising culturing the hematopoietic stem cells or hematopoietic progenitor cells in a medium containing at least one of the peptides set forth in any one of (I-1) to (I-3) or a pharmaceutically acceptable salt or solvate thereof.

(III) Mesenchymal Stem Cell Amplification Promoter and Use Thereof (III-1) A mesenchymal stem cell amplification promoter comprising at least one of the peptides set forth in any one of (I-1) to (I-3) or a pharmaceutically acceptable salt or solvate thereof as an active ingredient.

(III-2) A method for amplifying mesenchymal stem cells, comprising culturing the mesenchymal stem cells in a medium containing at least one of the peptides set forth in any one of (I-1) to (I-3) or a pharmaceutically acceptable salt or solvate thereof.

(IV) Hematopoietic Stem Cell Inducer and Use Thereof (IV-1) A hematopoietic stem cell inducer comprising at least one of the peptides set forth in any one of (I-1) to (I-3) or a pharmaceutically acceptable salt or solvate thereof.

(IV-2) The hematopoietic stem cell inducer according to (IV-1), which induces hematopoietic stem cells from pluripotent stem cells.

(IV-3) The hematopoietic stem cell inducer according to (IV-2), wherein the pluripotent stem cells are ES cells or iPS cells.

(IV-4) The hematopoietic stem cell inducer according to (IV-2), wherein the pluripotent stem cells are iPS cells that are derived from a patient and normalized by gene transfer, and the hematopoietic stem cells are used to treat the patient.

(IV-5) A method for inducing or producing hematopoietic stem cells, comprising culturing pluripotent stem cells or pluripotent stem cell-derived cells in a medium containing at least one of the peptides set forth in any one of (I-1) to (I-3) or a pharmaceutically acceptable salt or solvate thereof.

(IV-6) The method according to (IV-5), wherein the pluripotent cells are patient-derived iPS cells normalized by gene transfer.

(IV-7) The method according to (IV-5) or (IV-6), wherein the medium further contains at least one member selected from the group consisting of cell stimulatory factors, demethylating agents, and extracellular matrix proteins.

(IV-8) The method according to (IV-7), wherein the cell stimulatory factor is at least one member selected from the group consisting of stem cell stimulatory factors, thrombopoietin, interleukin-6, soluble interleukin-6 receptors, granulocyte colony-stimulating factors, interleukin-3, interleukin-11, and Flt3 ligand.

(V) Method for Amplifying Tissue-Specific Stem Cells or Tissue-Specific Progenitor Cells In Vitro (V-1) A method for growing tissue-specific stem cells or tissue-specific progenitor cells, comprising culturing the tissue-specific stem cells or tissue-specific progenitor cells in a medium containing at least one of the peptides set forth in any one of (I-1) to (I-3), or a pharmaceutically acceptable salt or solvate thereof, or containing the differentiation inhibitor set forth in (II-1) or the amplification promoter set forth in (III-1).

(V-2) The growth method according to (V-1), wherein the tissue-specific stem cells or tissue-specific progenitor cells are hematopoietic stem cells or hematopoietic progenitor cells, the method comprising amplifying the hematopoietic stem cells.

(V-3) The growth method according to (V-1), wherein the tissue-specific stem cells are mesenchymal stem cells, the method comprising amplifying the mesenchymal stem cells.

(V-4) The growth method according to any one of (V-1) to (V-3), wherein the medium further contains at least one member selected from the group consisting of cell stimulatory factors, demethylating agents, and extracellular matrix proteins.

(V-5) The growth method according to (V-4), wherein the cell stimulatory factor is at least one member selected from the group consisting of stem cell stimulatory factors, thrombopoietin, interleukin-6, soluble interleukin-6 receptors, granulocyte colony-stimulating factors, interleukin-3, interleukin-11, and Flt3 ligand.

(VI) Cell Population Including Hematopoietic Stem Cells or Hematopoietic Progenitor Cells, and Use Thereof (VI-1) A cell population including hematopoietic stem cells or hematopoietic progenitor cells obtained by the method set forth in any one of (IV-5) to (IV-8) or by the method set forth in any one of (V-1) to (V-5).

(VI-2) A pharmaceutical composition comprising the cell population set forth in (VI-1).

(VI-3) The pharmaceutical composition according to Item (VI-2), which is a hemopoietic function enhancer.

(VII) Antibody (VII-1) An antibody to at least one of the peptides set forth in any one of (I-1) to (I-3).

(VII-2) The antibody according to (VII-1), which is a monoclonal antibody.

(VII-3) The antibody according to (VII-1), which is a neutralizing antibody to at least one of the peptides set forth in any one of (I-1) to (I-3).

Advantageous Effects of Invention

The growth of hematopoietic stem cells or hematopoietic progenitor cells can be classified into "differential growth" associated with differentiation and maturation, and "autonomous growth" not associated with differentiation and maturation. The peptide of the present invention has an effect of preferentially inhibiting the "differential growth" of hematopoietic stem cells or hematopoietic progenitor cells. Accordingly, when hematopoietic stem cells (for example, autologous hematopoietic stem cells or umbilical cord blood hematopoietic stem cells with a relatively low immune response) or hematopoietic progenitor cells are cultured in the presence of the peptide of the present invention, preferably with a cell stimulatory factor, such as a cytokine, the absolute number of these cells can be increased by autonomous growth (amplification) in vitro, for example, in a test tube, while particularly inhibiting differentiation into myeloid cells. When mesenchymal stem cells that are believed to have an ability to differentiate into mesenchymal cells, such as osteoblasts, adipocytes, muscle cells, and chondrocytes, are cultured in the presence of the peptide of the present invention, preferably with a cell stimulatory factor, such as a cytokine, the number of these cells can be increased by in vitro autonomous growth (amplification), while inhibiting differentiation of the mesenchymal stem cells into the above-mentioned cells. Further, when pluripotent stem cells are cultured in the presence of the peptide of the present invention, preferably with a cell stimulatory factor, such as a cytokine, hematopoietic stem cells can be induced and produced in vitro while differentiation into myeloid cells is inhibited. Thus, these methods can achieve the objects of the present invention and solve the source problem of hematopoietic stem cells for transplantation in conventional hematopoietic stem cell transplantation therapy.

Further, the mechanism of differential growth and autonomous growth of hematopoietic stem cells can be analyzed by using the peptide of the present invention and an antibody to the peptide.

Figure 1:
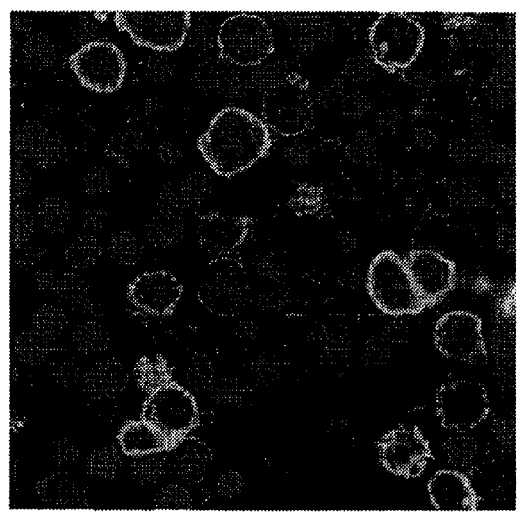
FIG. 1 shows an image of fetal mouse liver tissue (12.5 days of gestational age) immunostained with c-Kit antibody (R&D), DLK-1 antibody (MEL), and TOTO-3 (Invitrogen). In the image, sites stained in green are hematopoietic stem cells, sites stained in red are hepatoblasts, and sites stained in blue are nuclei.

DESCRIPTION OF EMBODIMENTS (I) Definition of the Terms Used Herein

In this specification, abbreviations for amino acid sequences, etc., are according to IUPAC-IUB recommendations (IUPAC-IUB Communication on Biological Nomenclature, Eur. J. Biochem., 138, 9 (1984)) and "Guidelines for the preparation of specifications which contain nucleotide and/or amino acid sequence" (Japanese Patent Office) and based on abbreviations conventionally used in the art.

The term "tissue-specific stem cells" as used herein refers to stem cells that have an ability to differentiate into a specific type of cells, such as hematopoietic cells, nerve cells, epithelial cells, epidermal cells, retinal cells, adipose tissue cells, and mesenchymal cells. Any of these stem cells has both "self-renewal ability" and "pluripotency". "Self-renewal ability" is an ability to grow while maintaining an undifferentiated state. "Pluripotency" is an ability to differentiate into specific types of cells. Examples of tissue-specific stem cells that can be preferably used in the present invention include hematopoietic stem cells and mesenchymal stem cells.

The term "hematopoietic stem cells" as used herein refers to cells that have both "self-renewal ability", i.e., an ability to grow while maintaining an undifferentiated state, and "pluripotency", i.e., an ability to differentiate into any type of blood or lymphoid cells, and that also have an ability to reconstitute hematopoiesis over a period of several months or longer.

Since a stem cell marker, CD34, is expressed in human hematopoietic stem cells, human hematopoietic stem cells can be characterized by CD34(+). Accordingly, CD34-positive cells can be used as human hematopoietic stem cells. In addition to CD34, other hematopoietic stem cell markers can also be used to characterize human hematopoietic stem cells, based on the cell surface antigen expressed on hematopoietic stem cells. Examples of hematopoietic stem cell markers including CD34 include Lin(−), CD34(+), CD38(−), DR(−), CD45(+), CD90(+), CD117(+), CD123(+), and CD133(+). Such markers can be used singly or in a combination of two or more. Specific examples of such combinations include a combination of Lin(−), CD34(+), and CD38(−), and a combination of CD45(+), CD34(+), and CD38(−). It is known that cell surface antigen expression on mouse hematopoietic stem cells changes between the fetal stage and adulthood. Examples of fetal hematopoietic stem cell markers include Lin(−), CD31(+), CD34(+), CD41(+), and c-Kit(+). Examples of adult hematopoietic stem cell markers include Lin(−), CD31(+), CD34(−/+), CD45(+), c-Kit(+), Sca-1 (+), CD150(+), and EPCR (+). These markers can be used singly or in a combination of two or more. Examples of such combinations include a combination of Lin(−), c-Kit(+), and Sca-1 (+), and a combination of CD45(+), c-Kit(+), and Sca-1 (+).

It has become clear that trace amounts of hematopoietic stem cells are contained in bone marrow, peripheral blood, and umbilical cord blood. Hematopoietic stem cells can be collected therefrom by using the above-mentioned stem cell marker as an indicator according to a known method, such as FACS (fluorescence activated cell sorting).

The term "mesenchymal stem cells" refers to stem cells that are believed to have an ability to differentiate into mesenchymal cells, such as osteoblasts, adipocytes, muscle cells, and chondrocytes.

The term "tissue-specific progenitor cells" refers to cells that are obtained by slightly differentiating but not terminally differentiating tissue-specific stem cells and that have "pluripotency" that is an ability to differentiate into specific types of cells, as with tissue-specific stem cells. Examples of tissue-specific progenitor cells that can be preferably used in the present invention include hematopoietic progenitor cells and mesenchymal progenitor cells. Hematopoietic progenitor cells are more preferable.

The term "hematopoietic progenitor cells" refers to cells that are derived from hematopoietic stem cells and that have not yet terminally differentiated. Hematopoietic progenitor cells can be classified into pluripotent hematopoietic progenitor cells and unipotent hematopoietic progenitor cells. Pluripotent hematopoietic progenitor cells can differentiate into blood cells of 2 or 3 lineages, and unipotent hematopoietic progenitor cells are limited to differentiating into one type of blood cell. Hematopoietic progenitor cells yield two types of progenitor cells: myeloid or lymphoid. Myeloid progenitor cells yield precursor cells that terminally differentiate into red blood cells, granulocytes (neutrophils, eosinophils, and basophils), monocytes, and megakaryocytes. Lymphoid progenitor cells yield precursor cells that terminally differentiate into T cells, B cells, and NK cells. Accordingly, hematopoietic progenitor cells can be precursors of myeloid cells (granulocytes (eosinophils, neutrophils, and basophils), monocytes, macrophages, mast cells, erythroid cells (red blood cells), megakaryocytic cells (megakaryocytes, platelets), and also precursors of lymphoid cells (T cells, B cells, and plasmocytes). The progenitors of these cell lineages can be classified by identifying cell markers using a per se known method. For example, CD13 is known as a myeloid cell marker. CD14 is known as a monocyte and macrophage marker. CD41 is known as a megakaryocytic marker. Glycophorin is known as an erythroid marker. CD19 is known as a B cell marker. CD3 is known as a T cell marker. Further, hematopoietic progenitor cells can be classified into cells corresponding to the following units: mixed colony-forming unit (CFU-Mix), which can differentiate into blood cells of multiple lineages; granulocyte-macrophage colony-forming unit (CFU-GM), which form colonies of neutrophils and macrophages; neutrophil colony-forming unit (DFU-G); colony forming unit-macrophage (CFU-M); colony forming unit-erythroid (CFU-E), which forms colonies and bursts of erythroid cells; burst forming unit-erythroid (BFU-E); colony forming unit-megakaryocyte (CFU-Meg), which form colonies and bursts of megakaryocytes; burst forming unit-megakaryocyte (BFU-Meg); and colony forming unit-eosinophil (CFU-Eo), colony forming unit-basophil (CFU-Baso), and colony forming unit-mast cell (CFU-Mast), which form colonies of eosinophils, basophils, and mast cells, respectively; etc. To which colony-forming unit the hematopoietic progenitor cell corresponds can be quantitatively determined by a colony assay method (in vitro colony method) known per se.

The term "pluripotent stem cells" refers to stem cells with pluripotency that is an ability to differentiate into various many types of cells. Such pluripotent stem cells have both "pluripotency" and "self-renewal ability", which is an ability to grow while maintaining the undifferentiated state. The pluripotent stem cells according to the present invention include embryonic stem cells (ES cells) and artificial pluripotent stem cells (iPS cells). As with embryonic stem cells, artificial pluripotent stem cells (iPS cells) have both "pluripotency" and "self-renewal ability", which are artificially imparted by transfer of several types of genes into somatic cells.

The term "pluripotent stem cell-derived cells" as used herein refers to cells that are obtained by slightly differentiating pluripotent stem cells and that have self-renewal ability and differentiation potential to differentiate into at least hematopoietic cells. Specific examples thereof include mesodermal cells.

The tissue-specific stem cells (e.g., hematopoietic stem cells and mesenchymal stem cells), tissue-specific progenitor cells (e.g., hematopoietic progenitor cells), and pluripotent stem cells according to the present invention are preferably vertebrate-derived cells, and more preferably cells derived from birds (e.g., chickens) or mammals (humans, mice, rats, rabbits, monkeys, chimpanzees, pigs, horses, goats, sheep, cows, dogs, cats, wallabies, or kangaroos). Cells derived from mammals are preferably used. Among the mammals, humans are preferable, as well as rodents (mice, rats, rabbits, etc.) that are widely used as test animals.

"Amplification" refers to increasing the number of cells that have not been terminally differentiated by cell division, whereas "growth" refers to increasing the total number of terminally differentiated cells and cells that have not been terminally differentiated. Accordingly, "amplification of tissue-specific stem cells" refers to increasing the number of tissue-specific stem cells with self-renewal ability and pluripotency by cell division. More specifically, amplification of tissue-specific stem cells means autonomous growth of tissue-specific stem cells while maintaining the undifferentiated state of the cells. As used herein, "growth of tissue-specific stem cells or tissue-specific progenitor cells" includes amplification of tissue-specific stem cells as mentioned above. Further, the growth includes growth of tissue-specific progenitor cells in a state that is not terminally differentiated. The growth of hematopoietic stem cells and hematopoietic progenitor cells can be assessed by analyzing a hematopoietic stem cell marker as mentioned above (for example, by counting the number of cells that correspond to CD34(+) by FACS) according to a quantitative analysis based on colony assay, etc. Furthermore, amplification of mesenchymal stem cells can be assessed by analyzing a mesenchymal stem cell marker (for example, by counting the number of cells that correspond to CD9, CD13, CD29, CD44, CD55, CD59, CD73, CD105, CD140b, CD166, and MHC Class I (+) by FACS) according to a quantitative analysis based on colony assay, etc. Examples of mesenchymal stem cells markers include VCAM-1, STRO-1, c-Kit, Sca-1, Nucleostemin, CDCP1, BMPR2, BMPR1A, and BPMR1B.

"Umbilical cord blood" refers to blood obtained from mammalian umbilical cord, preferably human umbilical cord. "Bone marrow-derived blood" refers to blood contained in cerebrospinal fluid present in mammalian bone marrow, preferably human bone marrow. Umbilical cord blood and bone marrow can be obtained from a cord blood bank and a bone marrow bank, respectively.

(II) Novel Peptide (Peptide of the Present Invention)

A feature of the peptide according to the present invention is having at least one of the following effects:

(1) an effect of inhibiting differentiation of hematopoietic stem cells or hematopoietic progenitor cells, preferably an effect of inhibiting differentiation of hematopoietic stem cells or hematopoietic progenitor cells into myeloid cells;

(2) an effect of promoting amplification of mesenchymal stem cells; and (3) an effect of inducing hematopoietic stem cells from pluripotent stem cells.

According to one embodiment of the peptide, the peptide comprises an amino acid sequence consisting of an amino acid residues shown below:

```
                                              (SEQ ID NO: 1)
     Cys Gln Lys Lys Asp Gly Pro Cys Val Ile

Asn Gly Ser.
```

This peptide comprises a partial sequence of the extracellular domain at positions 23 to 303 of human Dlk1 (delta-like 1 homolog) protein (SEQ ID NO: 11) that consists of 383 amino acid residues. For the sake of convenience, this peptide is hereinafter sometimes referred to as "KS-13".

The peptide according to the present invention includes peptides as set forth in the above amino acid sequence of KS-13 (SEQ ID NO: 1) wherein 1 or more, preferably about 1 to 6 amino acids are deleted, substituted, or added, the peptides having at least one of effects (1) to (3) above. Preferable are peptides that have (1) an effect of inhibiting the differentiation of hematopoietic stem cells or hematopoietic progenitor cells into myeloid cells, among the above-mentioned effects (1) to (3). More preferable are peptides that have effect (1) and one of effects (2) and (3). Still more preferable are peptides that have both effects (2) and (3) in addition to effect (1).

The peptide according to the present invention is as explained above. The peptide preferably contains amino acids that are identical or similar to those set forth in the amino acid sequence of SEQ ID NO: 1 at a percentage of 60% or more, preferably 75% or more, more preferably 80% or more, and even more preferably at least 85% or 90%. The percentage of "identity" or "similarity" as used herein can be determined by calculating the ratio of the number of overlapping identical or similar amino acids to the total number of amino acid residues in the amino acid sequence of SEQ ID NO: 1. The term "similar amino acids" as used herein refers to amino acids that are similar in physicochemical properties. For example, similar amino acids can be classified as follows: aromatic amino acids (Phe, Trp, Tyr); aliphatic amino acids (Ala, Leu, Ile, Val); polar amino acids (Gln, Asn); basic amino acids (Lys, Arg, His); acidic amino acids (Glu, Asp); hydroxy-containing amino acids (Ser, Thr); and amino acids with small side chains (Gly, Ala, Ser, Thr, Met). Substitution among such similar amino acids would probably hardly affect the properties of the peptide, and thus can be called "conservative amino acid substitution" in this sense (see, for example, Bowie et al., Science, 247: 1306-1310 (1990)).

When one or more amino acids in the amino acid sequence set forth in SEQ ID NO: 1 are substituted by other amino acids, or one or more amino acids are deleted or added, the position of substitution, deletion, or addition is not particularly limited, insofar as the resulting peptide has at least one of effects (1) to (3) above. Preferably, the peptide obtained by substitution, deletion, or addition has (1) an effect of inhibiting differentiation of hematopoietic stem cells or hematopoietic progenitor cells into myeloid cells. More preferably, the peptide has effect (1) and one of effects (2) and (3). Still more preferably, the peptide has both effects (2) and (3) in addition to effect (1).

Whether the peptide obtained by substitution, deletion, or addition has a differentiation inhibitory effect on hematopoietic stem cells or hematopoietic progenitor cells can be confirmed by assessing the effects on colony formation of the hematopoietic stem cells or hematopoietic progenitor cells, as described below in Experimental Example 9.

Further, whether the peptide obtained by substitution, deletion, or addition has an effect of promoting amplification of mesenchymal stem cells can be confirmed by assessing colony-forming unit-fibroblast (CFU-F). Furthermore, whether the peptide obtained by substitution, deletion, or addition has an effect of inducing hematopoietic stem cells from pluripotent stem cells can be confirmed by assessing the formation of HPP—CFC (high proliferative potential colony-forming cells) of the induced cells, the presence of LTC-IC (long-term culture-initiating cells), myeloid reconstituting ability of recipient mice after transplantation into the mice, and the presence of SCR(SCID-repopulating) cells in humans.

Examples of the peptide obtained by substitution, deletion, or addition include peptides represented by the following amino acid sequence and having at least one of the above-mentioned effects.

(SEQ ID NO: 2)
{(Cys XXa XXb)$_n$ XXc XXd}$_m$ Gly Pro Cys XXe

XXf Asn Gly Ser wherein XXa to XXf represent the following amino acid residues:
XXa: an amino acid residue of Gln or His;
XXb: an amino acid residue of His, Lys, Glu or Leu;
XXc: an amino acid residue of Lys or Met;
XXd: an amino acid residue of Ala, Asp, Glu, or Gln;
XXe: an amino acid residue of Val, Ala or Ile;
XXf: an amino acid residue of Ile, Met, or Val; and n and m independently represent an integer of 1 or 0 (provided, however, that all the following conditions are not simultaneously met: XXa is Gln, XXb is Lys, XXc is Lys, XXd is Asp, and XXe is Val, and XXf is Ile).

Specific examples of the peptide include a peptide corresponding to the above KS-13, which comprises a partial sequence of the extracellular domain region of a protein corresponding to the ortholog of human Dlk1 protein. For example, mouse Dlk1 protein corresponding to the ortholog of human Dlk1 protein has an amino acid sequence consisting of 385 amino acid residues (SEQ ID NO: 12). The region at positions 24 to 305 in the amino acid sequence of the mouse Dlk1 protein is an extracellular domain, and a partial sequence thereof (a sequence consisting of 13 amino acid residues at positions 124 to 136: SEQ ID NO: 3) is a peptide corresponding to KS-13.

Vertebrates such as mammals, for example, mice, rats, sewer rat, and like rodents; pigs, horses, goats, cows, wallabies, and macropus giganteus; zebra finches, platypus, turkeys, chickens, and like birds, have a Dlk1 protein corresponding to a human Dlk1 protein homolog or ortholog. Table 1 shows partial sequences corresponding to KS-13, which are located in extracellular domains of these Dlk1 proteins, and amino acid sequences of peptides corresponding to human-derived KS-13 and mouse KS-13. The amino acid residues that are conserved as well as in human-derived KS-13 are underlined.

TABLE 1

| Amino acid sequence of the peptide corresponding to KS-13 | Vertebrate from which DIK1 protein is derived | SEQ ID NO. |
|---|---|---|
| | Homo sapiens (human) | 1 |
| | Mus musculus (mouse), Rattus norvegicus (rat, sewer rat) | 3 |

TABLE 1-continued

| Amino acid sequence of the peptide corresponding to KS-13 | Vertebrate from which DIK1 protein is derived | SEQ ID NO. |
|---|---|---|
| Cys Gln Lys Lys Asp Gly Pro Cys Val Ile Asn Gly Ser | Sus scrofa (pig) | 4 |
| Cys Gln His Lys Ala Gly Pro Cys Val Ile Asn Gly Ser | Equus caballus (horse) | 5 |
| Cys Gln Lys Lys Asp Gly Pro Cys Val Met Asn Gly Ser | Capra hircus (goat), Bos Taurus (horse) | 6 |
| Cys Gln Lys Lys Asp Gly Pro Cys Ala Ile Asn Gly Ser | Macropus eugenii (wallaby) | 7 |
| Cys Gln Glu Met Asp Gly Pro Cys Val Val Asn Gly Ser | Monodelphis domestica (macropus giganteus) | 8 |
| Cys His Leu Lys Glu Gly Pro Cys Val Ile Asn Gly Ser Lys Glu Gly Pro Cys Val Ile Asn Gly Ser | Taeniopygia gatata (zebra finch) | 9 |
| Cys His Leu Lys Gln Gly Pro Cys Ile Ile Asn Gly Ser Gly Pro Cys Ile Ile Asn Gly Ser | Ornithorhynchus anatinus (platypus), Mekeagris gallopavo (turkey) Gallus gallus (chicken) | 10 |

For example, a comparison of the sequences of human and rodent (e.g., mouse or rat) peptides indicates that the third amino acid from the N terminus (corresponding to "XXb" in the amino acid sequence of SEQ ID NO: 2) may be either Lys or His, and the fifth amino acid (corresponding to "XXd" in the amino acid sequence of SEQ ID NO: 2) may be either Asp or Ala. Further, a comparison of the sequences of human and pig peptides indicates that the tenth amino acid from the N terminus (corresponding to "XXf" in the amino acid sequence of SEQ ID NO: 2) may be either Ile or Met. Further, a comparison of the sequences of human and macropus giganteus peptides indicates that three amino acids from the N terminus to position 3 may be deleted, and that the fifth amino acid from the N terminus (corresponding to "XXd" in the amino acid sequence of SEQ ID NO: 2) may be either Asp or Glu. Further, a comparison of the sequences of human and chicken peptides indicates that five amino acids from the N terminus to position 5 may be deleted, and that the ninth amino acid from the N terminus (corresponding to "XXe" in the amino acid sequence of SEQ ID NO: 2) may be either Val or Ile.

Among the peptides of the present invention, KS-13 is the most preferable peptide. However, as shown in SEQ ID NO: 2, any of 1 to 6 amino acids (XXa-XXf) in the amino acid sequence may be replaced by other amino acids. Alternatively, a peptide of the entire amino acid sequence minus one N-terminal or C-terminal amino acid, i.e., a peptide consisting of 12 amino acid residues may be used, or a peptide having one less amino acid, i.e., a peptide consisting of 11 amino acid residues may also be used. At most 5 amino acids, or 4 to 3 amino acids, at the N terminus may be deleted.

The peptide of the amino acid sequence set forth in SEQ ID NO: 1, wherein one or more amino acids are added includes, for example, a peptide wherein five, four, three, two, or one original human DIK1 protein-derived amino acid is added to the N terminus and/or C terminus of the amino acid sequence.

The method for substitution, addition, or deletion of one or more amino acids in the amino acid sequence of KS-13 (SEQ ID NO: 1) may be selected from methods commonly used in the art. For example, when the substitution, addition, or deletion is performed via DNA encoding the peptide, examples of usable methods include gene engineering techniques such as site-specific mutagenesis (Methods in Enzymology, 154, 350, 367-382-(1987); ibid. 100, 468 (1983); Nucleic Acids Res., 12, 9441 (1984); "Zoku Seikagaku Jikken Kouza 1", "Idenshi Kenkyuho II" edited by the Japanese Biochemical Society, p. 105 (1986)), chemical synthesis procedures such as the phosphotriester method and the phosphoamidite method (J. Am. Chem. Soc., 89, 4801 (1967); ibid. 91, 3350 (1969); Science, 150, 178 (1968); Tetrahedron Lett., 22, 1859 (1981); ibid. 24, 245 (1983)), and combinations thereof. More specifically, the DNA can also be synthesized by the phosphoramidite method or the phosphotriester method, and can also be synthesized using a commercially available automatic oligonucleotide synthesizer. A double-stranded fragment can be obtained from a chemically synthesized single-stranded product by synthesizing a complementary strand and annealing both of the strands under appropriate conditions, or by adding a complementary strand by using DNA polymerase together with an appropriate primer sequence. Furthermore, the peptide of the present invention can also be synthesized by a solid-phase synthesis method using a peptide synthesizer. When using a peptide synthesizer, the amino acid substitution, addition, or deletion can be easily performed by changing the type of protected amino acid. It is also possible to introduce a special amino acid, such as D-amino acid and sarcosine (N-methylglycine).

The peptide of the present invention may be in a free state, or in the form of a salt, or in the form of a solvate such as a hydrate. Examples of salts include physiologically acceptable, i.e., pharmaceutically acceptable, acid addition salts and base salts. Examples of such acid addition salts include inorganic acid salts such as hydrochloride, hydrobromate, nitrate, and sulfate; sulfonates such as methanesulfonate and toluenesulfonate; and organic acid salts such as trifluoroacetate and succinate. Examples of base salts include alkali metal salts such as salts of sodium, potassium, and lithium, and alkaline earth metal salts such as salts of calcium and magnesium.

The peptide of the present invention includes peptides wherein the C terminus is a carboxy group (—COOH), a carboxylate (—COO—), an amide (—CONH$_2$), or an ester (—COOR). The group represented by R in the ester may be, for example, an alkyl group containing 1 to 6 carbon atoms, such as methyl, ethyl, n-propyl, isopropyl, or n-butyl; a cycloalkyl group containing 3 to 8 carbon atoms, such as cyclopentyl or cyclohexyl; an aryl group containing 6 to 12 carbon atoms, such as phenyl or α-naphthyl; a phenyl-$C_{1-2}$ alkyl group, such as benzyl or phenethyl; a $C_{7-14}$ aralkyl group such as an α-naphthyl $C_{1-2}$ alkyl group, for example, a-naphthylmethyl; a pivaloyloxymethyl group; etc. When the peptide of the present invention has a carboxy group (or carboxylate) at a position other than the C terminus, a protein wherein the carboxyl group is amidated or esterified is also within the scope of the protein of the present invention. Further, the peptide of the present invention includes peptides wherein the amino group of the N-terminal amino acid residue is protected by a protecting group (e.g., a $C_{1-6}$ acyl group such as $C_{1-6}$ alkanoyl, such as a formyl group or an acetyl group), or modified with a fatty acid (a $C_{8-18}$ saturated fatty acid); peptides wherein the N-terminal glutamine residue, which is produced by cleavage in vivo, has been converted to pyroglutamic acid; peptides wherein a substituent (e.g., —OH, —SH, an amino group, an imidazole group, an indole group, a guanidino group, or the like) on an amino acid side chain in the molecule is protected by an appropriate protecting group (e.g., a $C_{1-6}$ acyl group such as a $C_{1-6}$alkanoyl group, such as a formyl group or an acetyl group); and complex peptides having a sugar chain bound thereto, such as what is called a glycoprotein; etc. Furthermore, the peptide of the present invention includes peptides wherein an imidazolyl group or a SH group is alkylated (e.g., methylated), aralkylated (e.g., benzylized), or acylated (e.g., acetylated, benzoylated). Examples of peptides modified with a fatty acid include myristoylated peptides wherein the amino acid of the N-terminal amino acid residue is modified with myristic acid.

(III) Hematopoietic Stem Cell or Hematopoietic Progenitor Cell Differentiation Inhibitor The peptide of the present invention thus obtained or a pharmaceutically acceptable salt or solvate thereof can be used as a hematopoietic stem cell or hematopoietic progenitor cell differentiation inhibitor as is or after being mixed with a cytophysiologically acceptable carrier and formulated into a composition as required. The peptides of the present invention may be used singly or in a combination of two or more. Human-derived KS-13 (SEQ ID NO: 1), rodent-derived peptide (SEQ ID NO: 3), pig-derived peptide (SEQ ID NO: 4), and chicken-derived peptide (SEQ ID NO: 10) are preferable. Human-derived KS-13 (SEQ ID NO: 1) and rodent-derived peptide (SEQ ID NO: 3) are more preferable.

The differentiation inhibitor can be prepared, for example, by dissolving the peptide of the present invention or a pharmaceutically acceptable salt or solvate thereof (hereinafter generically referred to as "the peptide of the invention") in water or an appropriate buffer (e.g., phosphate buffer, PBS, or tris-HCl buffer) to achieve an appropriate concentration. If necessary, preservatives, stabilizers, reducing agents, isotonizing agents, and the like in common use may be added.

The differentiation inhibitor of the present invention can be used, for example, by adding an effective amount of the peptide of the invention to a medium and culturing hematopoietic stem cells or hematopoietic progenitor cells to thereby grow the hematopoietic stem cells or hematopoietic progenitor cells. Thus, the present invention further provides a method for growing hematopoietic stem cells or hematopoietic progenitor cells, comprising culturing the hematopoietic stem cells or hematopoietic progenitor cells in the presence of the differentiation inhibitor of the present invention. The growth method includes the method for amplifying hematopoietic stem cells.

By culturing hematopoietic stem cells or hematopoietic progenitor cells in the presence of the peptide of the invention, these cells can be grown while differentiation is inhibited. Accordingly, the peptide of the present invention can also be used as a component of a reagent kit for in vitro growth of hematopoietic stem cells and hematopoietic progenitor cells.

(IV) Mesenchymal Stem Cell Amplification Promoter

The peptide of the present invention thus obtained or a pharmaceutically acceptable salt or solvate thereof can be used as a mesenchymal stem cell amplification promoter as is or after being mixed with a cytophysiologically acceptable carrier and formulated into a composition as required. The peptides of the present invention may be used singly or in any combination of two or more. Human-derived KS-13 (SEQ ID NO: 1), rodent-derived peptide (SEQ ID NO: 3), pig-derived peptide (SEQ ID NO: 4), and chicken-derived peptide (SEQ ID NO: 10) are preferable. Human-derived KS-13 (SEQ ID NO: 1) and rodent-derived peptide (SEQ ID NO: 3) are more preferable.

The cell amplification promoter can be prepared, for example, by dissolving the peptide of the present invention in water or an appropriate buffer (e.g., phosphate buffer, PBS, or tris-HCl buffer) to achieve an appropriate concentration. If necessary, preservatives, stabilizers, reducing agents, isotonizing agents, and the like in common use may be added.

The cell amplification promoter of the present invention can be used, for example, by adding an effective amount of the peptide of the invention to a medium, and culturing mesenchymal stem cells to thereby amplify the mesenchymal stem cells. Thus, the present invention further provides a method for amplifying mesenchymal stem cells, comprising culturing the mesenchymal stem cells in the presence of the peptide of the present invention or the amplification promoter of the present invention.

By culturing mesenchymal stem cells in the presence of the peptide of the invention, amplification of the cells can be promoted. Thus, the peptide of the present invention can also be used as a component of a reagent kit for in vitro growth of mesenchymal stem cells.

(V) Hematopoietic Stem Cell Inducer

The peptide of the present invention thus obtained or a pharmaceutically acceptable salt or solvate thereof (the peptide of the present invention) can be used as a hematopoietic stem cell inducer as is or after being mixed with a cytophysiologically acceptable carrier and formulated into a composition as required. The peptides of the present invention may be used singly or in any combination of two or more. Human-derived KS-13 (SEQ ID NO: 1), rodent-derived peptide (SEQ ID NO: 3), pig-derived peptide (SEQ ID NO: 4), and chicken-derived peptide (SEQ ID NO: 10) are preferable. Human-derived KS-13 (SEQ ID NO: 1) and rodent-derived peptide (SEQ ID NO: 3) are more preferable.

The inducer can be prepared, for example, by dissolving the peptide of the present invention in water or an appropriate buffer (e.g., phosphate buffer, PBS, or tris-HCl buffer) to achieve an appropriate concentration. If necessary, preservatives, stabilizers, reducing agents, isotonizing agents, and the like in common use may be added.

The inducer of the present invention can be used, for example, by adding an effective amount of the peptide of the invention to a medium and culturing pluripotent stem cells, such as embryonic stem cells (ES cells) or artificial pluripotent stem cells (iPS cells), to thereby induce and produce hematopoietic stem cells. Thus, the present invention further provides a method for inducing and producing hematopoietic stem cells, comprising culturing pluripotent stem cells in the presence of the peptide of the present invention or the inducer of the present invention.

By culturing pluripotent stem cells in the presence of the peptide of the invention, hematopoietic stem cells can be induced and produced. Accordingly, the peptide of the present invention can also be used as a component of a reagent kit for in vitro production of hematopoietic stem cells.

The iPS cells according to the present invention include healthy-person-derived iPS cells that are obtained from healthy persons and patient-derived iPS cells that are obtained from patients with some disease. Before culturing, the patient-derived iPS cells are preferably normalized by removing the cause of the disease by a recombinant technique, such as gene transfer. The hematopoietic stem cells induced and produced from such iPS cells by the method of the present invention are administered to the patient to treat the disease of the patient.

(VI) Method for In Vitro Growth of Tissue-Specific Stem Cells or Tissue-Specific Progenitor Cells (Method for Amplification of Tissue-Specific Stem Cells in a Test Tube)

The method for in vitro growth of tissue-specific stem cells or tissue-specific progenitor cells according to the present invention comprises culturing tissue-specific stem cells or tissue-specific progenitor cells in the presence of the peptide of the invention having at least one of the following effects: (1) an effect of inhibiting differentiation of hematopoietic stem cells or hematopoietic progenitor cells, and (2) an effect of promoting amplification of mesenchymal stem cells.

For example, hematopoietic stem cells and mesenchymal stem cells can be preferably used as tissue-specific stem cells, and hematopoietic progenitor cells can be preferably used as tissue-specific progenitor cells. Thus, the amplification method according to the present invention includes a method comprising culturing hematopoietic stem cells or hematopoietic progenitor cells in the presence of the peptide of the invention that has (1) an effect of inhibiting differentiation of hematopoietic stem cells or hematopoietic progenitor cells. The method of the present invention further includes a method comprising culturing mesenchymal stem cells in the presence of the peptide of the invention having (2) an effect of promoting amplification of mesenchymal stem cells.

The tissue-specific stem cells or tissue-specific progenitor cells that can be used in the method of the present invention include cell populations including at least tissue-specific stem cells or tissue-specific progenitor cells. Either tissue-specific stem cells or tissue-specific progenitor cells may be isolated and used, or both of the cells may be used. Alternatively, a cell population including at least either tissue-specific stem cells or tissue-specific progenitor cells and further including other cells may be used. A fraction containing tissue-specific stem cells or tissue-specific progenitor cells, which is obtained from a cell population including tissue-specific hematopoietic stem cells or tissue-specific progenitor cells, may also be used.

Examples of sources of tissue-specific stem cells or tissue-specific progenitor cells may be any tissue containing stem cells of vertebrates such as birds and mammals, and preferably mammals such as humans and rodents, such as mice and rats. For example, hematopoietic stem cells and hematopoietic progenitor cells can be obtained from a hematopoietic stem cell-containing fetal liver, fetal bone marrow, bone marrow, peripheral blood, umbilical cord blood, or peripheral blood from persons whose stem cells are mobilized by administration of a cytokine and/or an antitumor drug. Mesenchymal stem cells can be obtained from mesenchymal stem cell-containing bone marrow, umbilical cord, placenta, amnion, allantois, umbilical cord blood, gingiva, fat, muscle, and other mesenchyme-derived cells.

To culture tissue-specific stem cells or tissue-specific progenitor cells in the presence of the peptide of the present invention, a cultivation method using what is called a culture plate, a petri dish, or a flask can be used. However, when using a bioreactor that enables high density culture by mechanically controlling the medium composition, pH, etc., the culture system can be improved (Schwartz, Proc. Natl. Acad. Sci. USA. 88: 6760, 1991; Koller, M. R. Bio/Technology 11: 358, 1993; Koller, M. R. Blood 82: 378, 1993; Palsson, B. O. Bio/Technology 11: 368, 1993).

The medium used for cultivation is not particularly limited insofar as it does not interfere with the growth and survival of tissue-specific stem cells or tissue-specific progenitor cells. Preferable media for culturing hematopoietic stem cells or hematopoietic progenitor cells are, for example, a minimal essential medium (MEM) containing about 5% to about 20% fetal bovine serum, Dulbecco's modified Eagle's medium (DMEM), IMDM medium, RPMI 1640 medium, 199 medium, SF-02 medium (Sanko Junyaku), Opti-MEM medium (Gibco BRL), and X-VIVO 10 (Lonza), which is a medium for culturing hematopoietic stem cells/progenitor cells. Preferable media for culturing mesenchymal stem cells are, for example, a minimal essential medium (MEM) containing about 5% to about 20% fetal bovine serum, Dulbecco's modified Eagle's medium (DMEM), IMDM medium, RPMI 1640 medium, Opti-MEM medium (Gibco BRL), and the following media for culturing mesenchymal stem cells: MSCBM-CD (Lonza), MesenCult (Stem Cell Technologies), and MF medium (TM Cell Research Inc.). The pH of the medium is preferably about 6 to about 8.

If necessary, the medium may further contain cell stimulatory factors (cytokines), hormones such as insulin and hematopoietic hormones such as EPO (erythropoietin), differential growth control factors such as Wnt gene product (Thimoth, A. W., Blood, 89: 3624-3635-1997), transport proteins such as transferrin, demethylating agents such as 5azaD and TSA (Exp. Hematol. 34: 140, 2006), and extracellular matrix proteins such as fibronectin and collagen (Curr Opin Biotechnol. 2008 October; 19(5): 534-540; Cell 2007 June; 129(7): 1377-1388). In particular, when a cell stimulatory factor is added with the peptide of the present invention to the medium and hematopoietic stem cells or hematopoietic progenitor cells are cultured in the presence of the peptide of the present invention and the cell stimulatory factor, these cells can be grown while differentiation is inhibited. As a result, hematopoietic stem cells can be more efficiently amplified. The cell stimulatory factor refers to a factor that gives stimulation for growth, differentiation, survival, migration, etc., to tissue-specific stem cells or tissue-specific progenitor cells. Such a cell stimulatory factor is not particularly limited insofar as it does not inhibit growth of tissue-specific stem cells or tissue-specific progenitor cells. Specific examples thereof include SCF (stem cell growth factor), IL-3 (interleukin-3), GM-CSF (granulocyte/macrophage colony-stimulating factor), IL-6 (interleukin-6), soluble IL-6 receptor, IL-11 (interleukin-11), Flt-3L (fms-like tyrosine kinase-3 (Flt-3) ligand), EPO (erythropoietin), TPO (thrombopoietin), G-CSF (granulocyte colony-stimulating factor), TGF-β (transforming growth factor-β), MIP-1α (George, D., J. Exp. Med. 167: 1939-1944, 1988), Flt3/Flk2-ligand, FGF (fibroblast growth factor), etc. These stimulators are described in detail, for example, in Gallard, R. E., The cytokine facts book, Academic Press, 1994.

The cell stimulatory factors may be added to the medium singly or in a combination of two or more. Preferable cell stimulatory factors are, for example, SCF, G-CSF, IL-3, IL-6, sIL-6L, IL-11, Flt-3L, and TPO. SCF is especially essential.

Such a cell stimulatory factor is added to the medium in a concentration of 1 to 500 ng/mL, preferably 5 to 300 ng/mL, and more preferably 10 to 100 ng/mL.

For cultivation, the peptide of the present invention can be added to the medium to a final concentration of 1 to 500 μg/mL, preferably 5 to 300 μg/mL, and even more preferably 10 to 100 μg/mL. The tissue-specific stem cells or tissue-specific progenitor cells can be added to the medium to achieve a cell density in common use in the art. The cultivation is typically performed at about 30° C. to about 40° C. in an atmosphere of about 5 to about 10% $CO_2$ for a time sufficient to achieve the desired growth. The cultivation may be performed with aeration and stirring, if necessary.

(VII) Method for In Vitro Production of Hematopoietic Stem Cells (Method for Production of Hematopoietic Stem Cells in a Test Tube)

The method for inducing or producing hematopoietic stem cells according to the present invention comprises culturing pluripotent stem cells or pluripotent stem cell-derived cells in the presence of the peptide of the invention having (3) an effect of inducing hematopoietic stem cells from pluripotent stem cells.

The pluripotent stem cells that can be used in the method of the present invention include cell populations including embryonic stem cells (ES cells) and artificial pluripotent stem cells (iPS cells). The source of embryonic stem cells may be, for example, the inner cell mass of blastocysts of a vertebrate, such as birds and mammals, preferably mammals, such as humans and rodents such as mice and rats. The source of artificial pluripotent stem cells may be, for example, any type of tissue, such as skin and blood, of the above-mentioned vertebrates, preferably mammals.

The iPS cells according to the present invention include healthy-person-derived iPS cells obtained from healthy persons and patient-derived iPS cells obtained from patients with some disease. Prior to cultivation, the patient-derived iPS cells are preferably normalized by removing the cause of the disease by a recombinant technique, such as gene transfer. The hematopoietic stem cells induced and produced from such iPS cells by the method of the present invention are administered to the patient to treat the disease of the patient.

To culture pluripotent stem cells or pluripotent stem cell-derived cells in the presence of the peptide of the present invention, a cultivation method using what is called a culture plate, a petri dish, or a flask can be used. When using a bioreactor that enables high density culture by mechanically controlling the medium composition, pH, etc., the culture system can be improved (Schwartz, Proc. Natl. Acad. Sci. USA. 88: 6760, 1991; Koller, M. R. Bio/Technology 11: 358, 1993; Koller, M. R. Blood 82: 378, 1993; Palsson, B. O. Bio/Technology 11: 368, 1993).

The medium used for culturing is not particularly limited insofar as it does not interfere with the growth and survival of pluripotent stem cells, pluripotent stem cell-derived cells, hematopoietic stem cells, and hematopoietic progenitor cells. Preferable media are, for example, a minimal essential medium (MEM) containing about 5% to about 20% fetal bovine serum, Dulbecco's modified Eagle's medium (DMEM), IMDM medium, RPMI 1640 medium, 199 medium, SF-02 medium (Sanko Junyaku), Opti-MEM medium (Gibco BRL), and X-VIVO 10 (Lonza), which is a medium for culturing hematopoietic stem cells and hematopoietic progenitor cells. The pH of the medium is preferably about 6 to about 8.

If necessary, the medium may further contain cell stimulatory factors (cytokines), hormones such as insulin and hematopoietic hormones such as EPO (erythropoietin), differential growth control factors such as Wnt gene product (Thimoth, A. W., Blood, 89: 3624-3635-1997), transport proteins such as transferrin, demethylating agents such as SazaD and TSA (Exp. Hematol. 34: 140, 2006), extracellular matrix proteins such as fibronectin and collagen (Curr Opin Biotechnol. 2008 October; 19(5): 534-540; Cell 2007 June; 129(7): 1377-1388), L-glutamine, monothioglycerol, L-ascorbic acid, antibiotics, etc. In particular, when a cell stimulatory factor is added with the peptide of the present invention to the medium and pluripotent stem cells or pluripotent stem cell-derived cells are cultured in the presence of the peptide of the present invention and the cell stimulatory factor, differentiation of these cells into myeloid cells can be inhibited. As a result, differentiation into hematopoietic stem cells can be induced. The blood cell stimulatory factor refers to a factor that gives stimulation for growth, differentiation, survival, migration, etc, to hematopoietic cells. Such a cell stimulatory factor is not particularly limited insofar as it does not inhibit growth of hematopoietic stem cells or hematopoietic progenitor cells. Specific examples thereof include SCF, IL-3, GM-CSF, IL-6, soluble IL-6 receptor, IL-11, Flt-3L, EPO, TPO, G-CSF, TGF-β, MIP-1α (George, D., J. Exp. Med. 167: 1939-1944, 1988), and Flt3/Flk2-ligand. These stimulators are described in detail, for example, in Gallard, R. E., The cytokine facts book, Academic Press, 1994.

The cell stimulatory factors may be added to the medium singly or in a combination of two or more. Preferable cell stimulatory factors are, for example, SCF, G-CSF, IL-3, IL-6, sIL-6L, IL-11, Flt-3L, and TPO. SCF is especially essential. The concentration of the cell stimulatory factor added to the medium is 1 to 500 ng/mL, preferably 5 to 300 ng/mL, and more preferably 10 to 100 ng/mL.

For cultivation, the peptide of the present invention can be added to the medium to a final concentration of 1 to 500 μg/mL, preferably 5 to 300 μg/mL, and more preferably 10 to 100 μg/mL. The pluripotent stem cells or pluripotent stem cell-derived cells can be added to the medium to achieve a cell density in common use in the art. The cultivation is typically performed at about 30° C. to about 40° C. in an atmosphere of about 5 to about 10% $CO_2$ for a time sufficient to achieve the desired amplification. The cultivation may be performed with aeration and stirring, if necessary.

For cultivation, the peptide of the present invention can be added to the medium to a final concentration of 1 to 500 μg/mL, preferably 5 to 300 μg/mL, and more preferably 10 to 100 μg/mL. The pluripotent stem cells or pluripotent stem cell-derived cells can be added to the medium to achieve a cell density in common use in the art. The cultivation is typically performed at about 30° C. to about 40° C. in an atmosphere of about 5 to about 10% $CO_2$ for a time sufficient to achieve the desired amplification. The cultivation may be performed with aeration and stirring, if necessary.

(VIII) Cell Population Including Hematopoietic Stem Cells or Hematopoietic Progenitor Cells Obtained by the Amplification and Production Methods of the Present Invention, and Use Thereof.

"The cell population including hematopoietic stem cells or hematopoietic progenitor cells" obtained by the amplification method (V) or production method (VI) of the present invention can be used as a composition (a graft) for blood cell transplantation in place of conventional bone marrow transplantation or cord blood transplantation.

As used herein, the "cell population including hematopoietic stem cells or hematopoietic progenitor cells" (hereinafter sometimes simply referred to as "cell population") refers to a cell population including hematopoietic stem cells obtained by the amplification method (V) or production method (VI) of the present invention; isolation and purification of hematopoietic stem cells alone are not necessarily required. In general, ex vivo production of hematopoietic cells from pluripotent stem cells and pluripotent stem cell-derived cells fails to produce hematopoietic stem cells alone in a pure form. The obtained cell population is known to include mesodermal, ectodermal, and endodermal cells of various stages of differentiation. Each of these cell populations can be purified and collected by flow cytometry. After the obtained hematopoietic stem cells have been purified and collected, these cell populations can be transplanted for therapeutic purposes. Further, ex vivo production or growth of hematopoietic stem cells fails to produce hematopoietic stem cells alone in a pure form, and the obtained cell population is known to include myeloid and lymphoid cells of all stages of differentiation. However, these cells are also vital for a living organism, and administration of the entire proliferated cell population is expected to improve hematogenous functions. In particular, in cell transplantation for treating mammals with impaired hematopoiesis, quick hematopoiesis improvement effects are required. Accordingly, transplantation of a non-uniform cell population including somewhat differentiated blood cells of multiple lineages, rather than uniform undifferentiated hematopoietic stem cells, would provide better therapeutic effects. Of course, a uniform hematopoietic stem cell population consisting only of undifferentiated hematopoietic stem cells is also within the scope of the cell population. Such a uniform cell population can be obtained from the above-mentioned non-uniform cell population by a per se known method, such as FACS.

The cell population produced and amplified by the method of the present invention can be used in combination with total body X-ray irradiation therapy or advanced chemotherapy for leukemia, and is also usable for various other diseases. For example, when a therapy that causes myelosuppression as a side effect, such as chemotherapy or radiation therapy, is performed, if bone marrow is collected from a patient with solid cancer before the therapy and hematopoietic stem cells or hematopoietic progenitor cells are amplified in vitro and returned to the patient after the therapy, the patient's early recovery from hematopoiesis impairment due to the side effect can be expected, which enables stronger chemotherapy, thus improving therapeutic effects of chemotherapy. Further, the cell population of the present invention can be used as a preventive and/or therapeutic agent for the following diseases: diseases associated with impaired hematopoiesis, such as aplastic anemia, congenital immune deficiency, inborn errors of metabolism, myelodysplastic syndromes, leukemia, malignant lymphoma, multiple myeloma, myelofibrosis, chronic granulomatous disease, duplicated immunodeficiency syndrome, agammaglobulinemia, Wiskott-Aldrich syndrome, acquired immune deficiency syndrome (AIDS) and like immunodeficiency syndromes, thalassemia, hemolytic anemia due to an enzyme defect, sicklemia and like congenital anemia, Gaucher's disease, mucopolysaccharidosis and like lysosomal storage diseases, adrenoleukodystrophy, etc.

This cell population can also be used after being formulated into a pharmaceutical composition by optionally mixing a pharmacologically acceptable carrier and/or a buffer in addition to the hematopoietic stem cells and/or hematopoietic progenitor cells that are grown or produced by the method of the present invention.

Various organic or inorganic carrier materials in common use as materials for formulating pharmaceuticals can be used as the pharmacologically acceptable carrier. Such materials can be used, for example, as suspending agents in suspensions, isotonizing agents, buffering agents, soothing agents, etc. Pharmaceutical additives such as preservatives, antioxidants, thickeners, and stabilizers can also be used as required.

The transplantation (administration) of the cell population or the pharmaceutical composition prepared therefrom can be performed in the same manner as conventional bone marrow transplantation or cord blood transplantation. For example, parenteral administration (e.g., intravenous injection or topical injection) can be used. Preferable pharmaceutical preparations include, for example, aqueous and non-aqueous isotonic sterile injectable liquids.

Although the dosage of the cell population or the pharmaceutical composition prepared therefrom according to the present invention may vary depending on the activity of the peptide of the present invention, severity of disease, recipient animal species, the recipient's drug tolerance, sex, body weight, age, etc., the amount of hematopoietic stem cells per dose for an adult is typically $1\times10^6$ cells/kg or more, preferably $1\times10^6$ cells/kg to $1\times10^{10}$ cells/kg, and more preferably $2\times10^6$ cells/kg to $1\times10^9$ cells/kg.

(IX) Antibody to the Peptide of the Present Invention

The present invention further provides an antibody to the peptide of the present invention.

The antibody of the present invention includes polyclonal antibodies and monoclonal antibodies. Monoclonal antibodies are preferable.

A preferable antibody is, for example, an antibody to KS-13 (SEQ ID NO: 2) (anti-KS-13 antibody) among the peptides of the present invention. The monoclonal antibody of the present invention belongs to an immunoglobulin class and subclass of a vertebrate, such as birds and mammals, including rodents, and preferably mammals such as humans, mice, or rats. Although the antibody may be of any immunoglobulin class and subclass thereof, a preferable class and subclass thereof is immunoglobulin M(IgM), and more preferably IgM (K chain).

The monoclonal antibody can be produced according to a known method, such as the method described in Molecular Cloning, A Laboratory Manual, Second Edition (Cold Spring Harbor Laboratory Press, 1989). A specific production process will be described in Example 2 below. The monoclonal antibody of the present invention is preferably a humanized antibody in view of reducing antigenicity to humans. The humanized antibody is a chimeric antibody produced by replacing a portion other than the variable region (hypervariable region) of a non-human animal antibody with the amino acid sequence of a human immunoglobulin. It is an antibody that has reduced antigenicity to humans, while retaining its affinity for the peptide of the present invention, particularly KS-13. The humanized monoclonal antibody can be produced according to a known method.

EXAMPLES

Hereinafter, the present invention is described in detail with reference to examples and experimental examples. However, the present invention is not limited to these experimental examples.

There are two types of phenomena in which cells are divided and the number of cells increases: "differential growth" associated with differentiation and maturation, and "autonomous growth" not associated with differentiation or maturation. Therefore, in the following experimental examples, the former is referred to as "differential growth,"

and the latter is referred to as "autonomous growth" (corresponding to "amplification" referred to in the present invention).

Example 1

Preparation of Peptide

As shown in FIG. 1, because hematopoietic stem cells (stained in green in the figure) are located near hepatoblasts (stained in red in the figure) in the liver in the embryo, hepatoblasts are considered to play an important role in the amplification of hematopoietic stem cells. Accordingly, in order to purify and collect hepatoblasts, an attempt was made to prepare antibodies that can be used in flow cytometry. From among multiple proteins expressed on the cell membrane of hepatoblasts, 10 types of peptides corresponding to the ectodomain and having high homology with both mouse and human were designed (hereinafter referred to as peptides A-J), and anti-peptide antibodies were prepared.

```
A: cqkkdgpcvings
                                       (SEQ ID NO: 1)
Cys Gln Lys Lys Asp Gly Pro Cys Val Ile Asn Gly Ser B: yecscapgysgkd
                                       (SEQ ID NO: 13)
Tyr Glu Cys Ser Cys Ala Pro Gly Tyr Ser Gly Lys Asp C: pcqhggtcvddeg
                                       (SEQ ID NO: 14)
Pro Cys Gly His Gly Gly Thr Cys Val Asp Asp Glu Gly D: canngtcvsldgl
                                       (SEQ ID NO: 15)
Cys Ala Asn Asn Gly Thr Cys Val Ser Leu Asp Gly Leu E: rashasclcppgf
                                       (SEQ ID NO: 16)
Arg Ala Ser His Ala Ser Cys Leu Cys Pro Pro Gly Phe F: lcdrdvracssap
                                       (SEQ ID NO: 17)
Leu Cys Asp Arg Asp Val Arg Ala Cys Ser Ser Ala Pro G: sgnfceivansct
                                       (SEQ ID NO: 18)
Ser Gly Asn Phe Cys Glu Ile Val Ala Asn Ser Cys Thr H: pgqcictdgwdge
                                       (SEQ ID NO: 19)
Pro Gly Gly Cys Ile Cys Thr Asp Gly Trp Asp Gly Glu I: pnpcendgvctdi
                                       (SEQ ID NO: 20)
Pro Asn Pro Cys Glu Asn Asp Gly Val Cys Thr Asp Ile J: vtspgclhglcge
```

```
                                       (SEQ ID NO: 21)
Val Thr Ser Pro Gly Cys Leu His Gly Leu Cys

Gly Glu.
```

In accordance with the routine method of antibody preparation, these peptides were separately injected into rats for immunization, and lymph node cells were collected. After cell fusion, ELISA was performed. As a result, in regard to peptide A, a positive reaction was observed with about 70% of the prepared antibodies. However, in regard to the peptides other than peptide A, a positive reaction was observed with only 10% or less of the prepared antibodies.

The above results suggested that peptide A (SEQ ID NO: 2) has some kind of physiological activity. This was named KS-13 (consisting of 13 amino acids) and used in the following experiments.

Example 2

Preparation of Anti-KS-13 Antibody (1) Immunization of Rats and Measurement of Antibody Titer In order to prepare an antibody against KS-13 (anti-KS-13 antibody), rats were immunized four times at 2-week intervals in accordance with the routine method, using a peptide consisting of 12 amino acid residues (Cys at the N-terminal of KS-13 was deleted) as a peptide easily recognizable as an antigen and using KLH (keyhole limpet hemocyanin) as a carrier protein. Subsequently, the antibody titer was measured by ELISA using HRP-labeled anti-rat IgG. As a result, a sufficient increase in the antibody titer was observed.

(2) Individual Screening

Using 3 rats (No. 1, No. 2, and No. 3), serum was collected before immunization and after immunization using the above-described peptide and carrier protein. Hereinafter, the experiment in which the serum before immunization was used is referred to as a control.

A hematopoietic stem cell population (Sca-1 (+)c-Kit(+) CD45(+) cells) was collected at 1,000 cells/well from the fetal mouse liver (12.5 days of gestational age). These cells were added to a medium (X-VIVO10) containing cell stimulatory factors (SCF, IL-3, IL-6, G-CSF, and GM-CSF), together with KS-13 and the above-mentioned serum (1.5 to 10%), and cultured for 8 days. After culturing, the total number of cells was measured. The serum of rat (No. 2) in which the total number of cells was significantly increased compared to the control was assumed to be neutralizing the differentiation inhibitory effect of KS-13.

(3) Fusion

In accordance with the report by Kohler G. and Milstein C. (Nature 1975; 256: pp. 495-497), spleen cells of the immunized rat (No. 2) in which increased antibody titers and KS-13 neutralizing activity were observed were fused with myeloma cells (p3U1), using the polyethylene glycol method. In accordance with the routine method, an antigen-coated plate in which KS-13 was bound to a maleimide-activated plate (Pierce) was used to screen the culture supernatant using the antibody titer thereof as an index, and 5 cell lines having a positive antibody titer were selected. These cell lines having a positive antibody titer were further screened by a similar method as in the individual screening described above, and 3 lines (51-2, 5-2, and 5-3) in which KS-13 neutralizing activity was observed were selected.

(4) Final Screening and Confirmation of Subclass

The thus-obtained 3 cell lines were cloned by the limiting dilution method, and the antibody production was confirmed by ELISA. Ultimately, 6 cell lines (51-2-1, 51-2-2, 5-2-1, 5-2-2, 5-3-1, and 5-3-2) were then obtained. Subclasses of the established cell lines were identified using a rat monoclonal isotyping kit (Serotec), and it was found that the subclass of all of these cell lines was IgM (κ chain).

Experimental Example 1

Hematopoietic Colony-Forming Cell Assay

KS-13 (10 μg/mL or 30 μg/mL) was added to a semisolid medium (Methocult M3434 produced by STEMCELL Technologies) containing cell stimulatory factors (50 ng/mL of rm SCF, 10 ng/mL of rm IL-3, 10 ng/mL of rh IL-6, and 3 U/mL of rh EPO) (rm: recombinant form; rh: recombinant human form), and mouse fetal liver hematopoietic stem cells (CD45(+)c-Kit(+)Sca-1 (+)) (1,000 cells/dish) were cultured. Hematopoietic colony-forming cell assay was performed to evaluate the hematopoietic potential of the cells. Further, for comparison, hematopoietic colony-forming cell assay was performed in a similar manner using a KS-13-free liquid medium (none), and the hematopoietic potential of the cells was evaluated.

Figure 2:
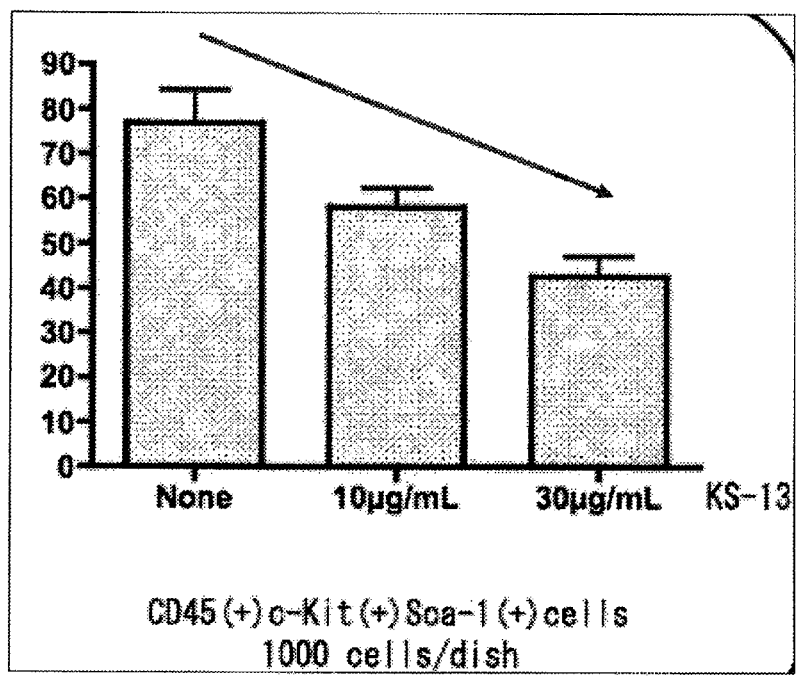
FIG. 2 shows the results of hematopoietic colony-forming cell assay of mouse fetal liver hematopoietic stem cells (CD45(+)c-Kit(+)Sca-1(+)) using a KS-13 (10 μg/mL and 30 μg/mL)-containing semisolid medium or KS-13-free medium in the presence of cell stimulatory factors (50 ng/mL of rm SCF, 10 ng/mL of rm IL-3, 10 ng/mL of rh IL-6, and 3 U/mL of rh EPO) (Experimental Example 1). (A) shows the number of colonies formed after culturing for 12 days in each experimental system. The vertical axis indicates the number of colonies. (B) shows images showing the morphology (the size) of mixed colonies formed after culturing for 1 month (left side: KS-13-free medium; right side: KS-13 (30 μg/mL)-containing medium).
Figure 2:
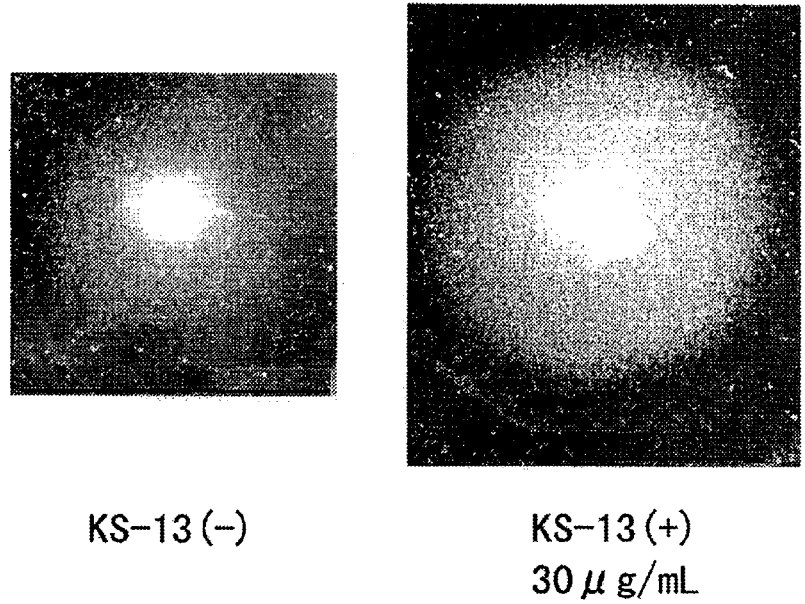

FIG. 2(A) shows the results of measurement of the number of colonies formed after culturing for 12 days. FIG. 2(B) shows the results of observation of the morphology of mixed colonies (in the absence of KS-13 and in the presence of KS-13 (30 μg/mL)) that were formed after prolonged culturing for 1 month. As is clear from FIG. 2(A), regardless of the presence of cell stimulatory factors, dose-dependent inhibition of hematopoietic colony formation was confirmed in the presence of KS-13 in an amount of 10 μg/mL and 30 μg/mL. This suggested that KS-13 inhibits differential growth or autonomous growth of hematopoietic stem cells (CD45(+)c-Kit(+)Sca-1 (+)) in the presence of cell stimulatory factors.

Further, as is clear from FIG. 2(B), when the cells were cultured for a long time (1 month) in the presence of KS-13, a tendency of increase in the size of mixed colonies was observed, in comparison to the case of the absence of KS-13. This suggested that KS-13 may inhibit differential growth, rather than autonomous growth, of hematopoietic stem cells (CD45(+)$_c$— Kit(+)Sca-1 (+)) in the presence of cell stimulatory factors.

Experimental Example 2

Amplification of Human Cord Blood CD34(+) Hematopoietic Stem Cells by the Addition of KS-13

(1) Experimental Method (1-1) in vitro amplification of a human cord blood CD34(+) hematopoietic stem cell population (cell population in which hematopoietic stem cells and slightly differentiated hematopoietic progenitor cells are mixed) was attempted by culturing the population in a KS-13-containing (1 μg/mL and 10 μg/mL) liquid medium (serum-free synthetic medium for lymphocytes (X-VIVO 10: Takara) to which SCF (50 ng/mL), TPO (10 ng/mL), and Flt3L (20 ng/mL) were added). As a control test (control), a serum-free synthetic medium for lymphocytes (X-VIVO 10: Takara)) to which a KS-13-free liquid medium (SCF (50 ng/mL), TPO (10 ng/mL), Flt3L (20 ng/mL)) was added was used. Additionally, as a comparative test (positive control), a liquid medium (X-VIVO 10: Takara) to which a mixture of various cell stimulatory factors (full: 50 ng/mL of SCF, 10 ng/mL of TPO, 20 ng/mL of Flt3L, 20 ng/mL of IL-6, and 20 ng/mL of sIL-6R) was added was used. In each medium, a human cord blood CD34(+) hematopoietic stem cell population was cultured, and the total number of cells, the number of CD34(+) cells (the number of hematopoietic stem cells and slightly differentiated hematopoietic progenitor cells), and the number of CD34(−) cells (the number of differentiated mature blood cells) were measured at the start of cultivation (day 0 of culturing) as well as at day 7 and day 11 of culturing. The cell stimulatory factors used in the positive control are factors that are used in the existing human CD34(+) cell amplification method, and it has been reported that these factors act on the growth of human hematopoietic stem cells (Sui X, et al., Proc Natl Acad Sci USA, 1995, 92, 2859-2863; Ebihara Y, et al., Blood 1997, 90, 4363-4368).

(1-2) In order to confirm induction of cell death, cells that were liquid-cultured for 11 days in each experimental system were stained with PI, and the ratio of live cells was calculated based on the measured number of dead cells.

(1-3) At day 11 of culturing, colony-forming cell assay was further performed in accordance with the routine method to count the number of various hematopoietic progenitor cells (CFU-GEMM (colony-forming unit-granulocyte/erythrocyte/macrophage/megakaryocyte), BFU-E (burst-forming unit-erythrocyte), CFU-GM (colony-forming unit-granulocyte/macrophage), CFU-M (colony-forming unit-macrophage), and CFU-G (colony-forming unit-granulocyte)).

(2) Experimental Results

Figure 3:
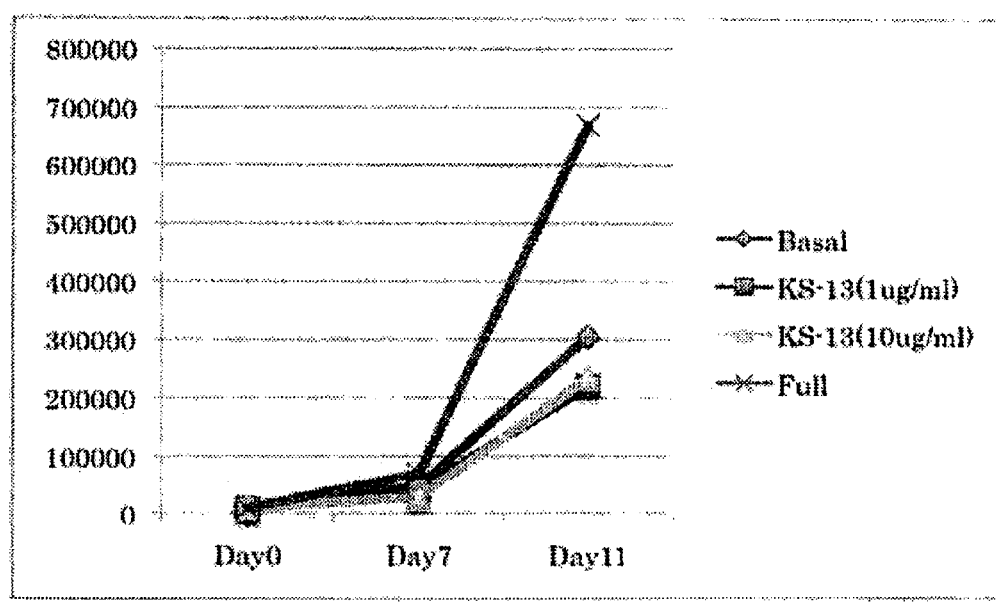
FIG. 3 shows the result obtained by measuring the total number of cells over time by culturing a human cord blood CD34(+) hematopoietic stem cell population in a medium (basal) containing cell stimulatory factors (50 ng/mL of SCF, 10 ng/mL of TPO, and 20 ng/mL of Flt3L), a medium (full) containing a cell stimulatory factor mixture (50 ng/mL of SCF, 10 ng/mL of TPO, 20 ng/mL of Flt3L, 20 ng/mL of IL-6, and 20 ng/mL of sIL-6R), a medium (KS-13 (1 μg/mL)) containing 1 μg/mL of KS-13, and a medium (KS-13 (10 μg/mL)) containing 10 μg/mL of KS-13 (day 0: the start of cultivation; day 7: day 7 of culturing; and day 11: day 11 of culturing) (Experimental Example 2).
Figure 4:
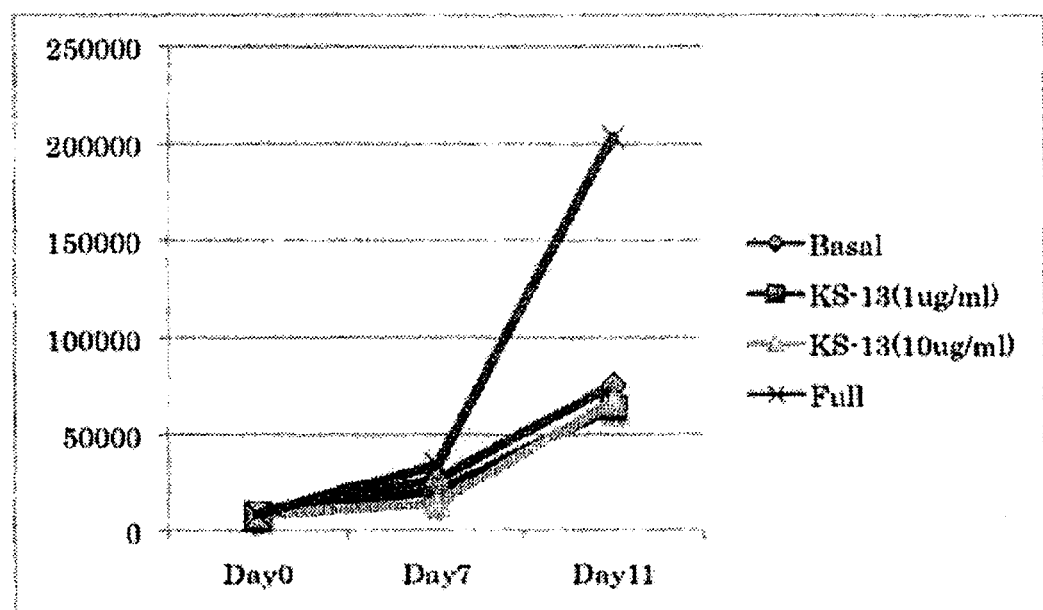
FIG. 4 shows the result obtained by measuring the number of CD34(+) cells over time by culturing a human cord blood CD34(+) hematopoietic stem cell population in a medium (basal) containing cell stimulatory factors (50 ng/mL of SCF, 10 ng/mL of TPO, and 20 ng/mL of Flt3L), medium (full) containing a cell stimulatory factor mixture (50 ng/mL of SCF, 10 ng/mL of TPO, 20 ng/mL of Flt3L, 20 ng/mL of IL-6, and 20 ng/mL of sIL-6R), medium (KS-13 (1 μg/mL)) containing 1 μg/mL of KS-13, and medium (KS-13 (10 μg/mL)) containing 10 μg/mL of KS-13 (day 0: the start of cultivation; day 7: day 7 of culturing; and day 11: day 11 of culturing) (Experimental Example 2).
Figure 5:
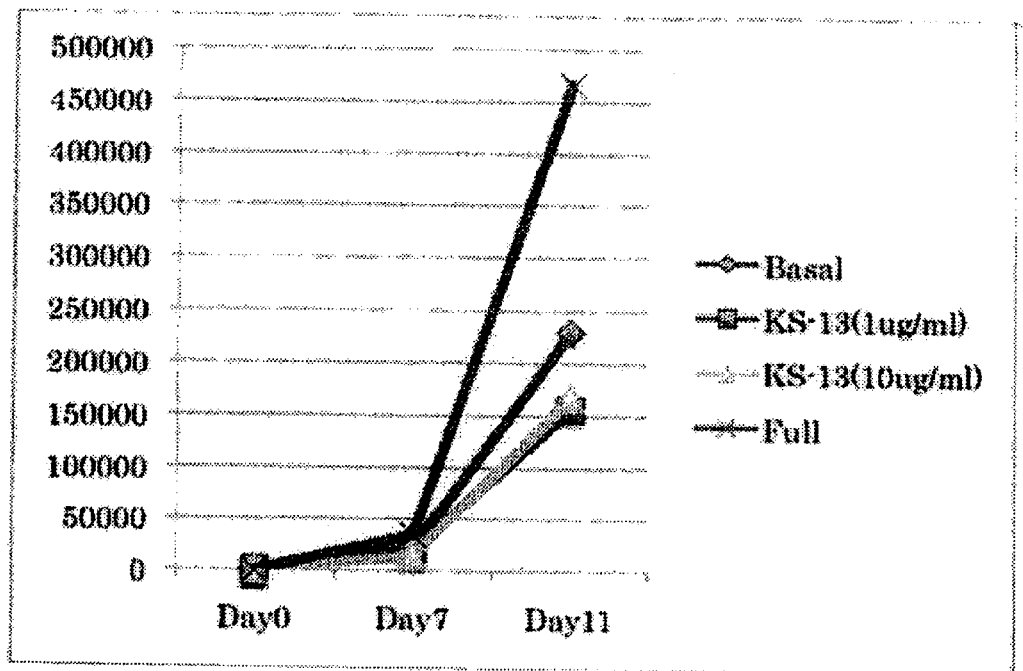
FIG. 5 shows the result obtained by measuring the number of CD34(−) cells over time by culturing a human cord blood CD34(+) hematopoietic stem cell population in a medium (basal) containing cell stimulatory factors (50 ng/mL of SCF, 10 ng/mL of TPO, and 20 ng/mL of Flt3L), medium (full) containing a cell stimulatory factor mixture (50 ng/mL of SCF, 10 ng/mL of TPO, 20 ng/mL of Flt3L, 20 ng/mL of IL-6, and 20 ng/mL of sIL-6R), medium (KS-13 (1 μg/mL)) containing 1 μg/mL of KS-13, and medium (KS-13 (10 μg/mL)) containing 10 μg/mL of KS-13 (day 0: the start of cultivation; day 7: day 7 of culturing; and day 11: day 11 of culturing) (Experimental Example 2).

FIGS. 3, 4, and 5 show changes over time in the total number of cells, number of CD34(+) cells, and number of CD34(−) cells, respectively.

(2-1) Changes Over Time in the Total Number of Cells

As shown in FIG. 3, the total number of cells obtained when a human cord blood CD34(+) hematopoietic stem cell population was cultured for 11 days in the presence of KS-13 (1 μg/mL and 10 μg/mL) increased from the start of cultivation (day 0) (KS-13 (1 μg/mL): 27.50-fold increase; KS-13 (10 μg/mL): 29.38-fold increase); however, the rate of increase was lower compared to the positive control (full: cultured in the presence of cell stimulatory factors) and the control (basal). The rate of increase in the total number of cells obtained by culturing for 11 days in each cultivation system (control, positive control, KS-13 (1 μg/mL) added, and KS-13 (10 μg/mL) added) is as follows when the rate of increase in the control is assumed to be 1.

Rate of Increase in the Total Number of Cells Control: positive control:KS-13(1 μg/mL):KS-13(10 μg/mL)=1:2.2:0.72:0.77. [Math. 1]

This shows that unlike cell stimulatory factors, KS-13 does not have cell differential growth activity. When human CD34 (+) cells were cultured under control (basal) conditions, it is assumed that both differential growth and autonomous growth would be observed; however, from the above results, KS-13 is believed to inhibit either or both differential growth and autonomous growth (amplification) (differentiation inhibitory effect and amplification inhibitory effect).

(2-2) Changes Over Time in the Number of CD34(+) Cells

As shown in FIG. 4, when a human cord blood CD34(+) hematopoietic stem cell population was cultured for 11 days in the presence of KS-13 (1 μg/mL and 10 μg/mL), the number of CD34(+) cells (hematopoietic stem cells and slightly differentiated hematopoietic progenitor cells) increased about 8-fold (KS-13 (1 μg/ml): 7.96-fold; KS-13 (10 μg/ml): 8.38-fold) from the start of cultivation (day 0), although the rate of increase was considerably lower compared to the positive control (indicated as "Full" in the figure).

The rate of increase in the number of CD34(+) cells in each cultivation system (control, positive control, KS-13 (1 μg/mL), and KS-13 (10 μg/mL)) is as follows when the rate of increase in the control is assumed to be 1.

Rate of increase in the number of CD34(+) cells Control:positive control:KS-13(1 μg/mL): KS-13(10 μg/m)=1:2.69:0.84:0.89. [Math. 2]

(2-3) Changes over Time in the Number of CD34(−) Cells

As shown in FIG. 5, CD34(−) cells (differentiated mature blood cells) were not present at the time of cell seeding in any of the experimental systems (control, positive control, KS-13 (1 μg/mL), and KS-13 (10 μg/mL)). However, when a human cord blood CD34(+) hematopoietic stem cell population was cultured for 11 days, the generation of CD34(−) cells and an increase in the number of cells were observed in all of the experimental systems.

The rate of increase of the number of CD34(−) cells in each experimental system (control, positive control, KS-13 (1 μg/mL), and KS-13 (10 μg/mL)) is as follows when the rate of increase in the control is assumed to be 1.

The rate of increase in the number of CD34(−) cells Control:positive control:KS-13(1 μg/mL): KS-13 (10 μg/m)=1:2.04:0.68:0.73. [Math. 3]

As shown in the above Math 2 and Math 3, when a human cord blood CD34(+) hematopoietic stem cell population was cultured for 11 days in the presence of KS-13 (1 μg/mL and 10 μg/mL), the rate of increase in the number of CD34(+) cells and the rate of increase in the number of CD34(−) cells were both lower compared to the control, and the rate of increase in the number of CD34(−) cells was lower than the rate of increase in the number of CD34(+) cells. This means that the addition of KS-13 inhibits an increase in CD34(−) cells (differentiated mature blood cells) more strongly than it inhibits an increase in CD34(+) cells (hematopoietic stem cells and hematopoietic progenitor cells). While the section (2-1) showed that KS-13 has either or both amplification inhibitory effect and differentiation inhibitory effect on hematopoietic stem cells and hematopoietic progenitor cells, the above results show that the differentiation inhibitory effect is dominant to the amplification inhibitory effect.

As described above, in the positive control that used the cell stimulatory factors used in the existing human CD34(+) cell amplification method, a significant increase in blood cells (i.e., CD34(−) cells) was observed simultaneously with the growth of CD34(+) cells, i.e., hematopoietic stem cells and hematopoietic progenitor cells, thus confirming promotion of differential growth of hematopoietic stem cells and hematopoietic progenitor cells.

(2-4) Confirmation of Induction of Cell Death

The live cell ratio {(the number of live cells/(the number of live cells+the number of dead cells)} was calculated for each experimental system (control, positive control, KS-13 (1 μg/mL), and KS-13 (10 μg/mL)), using cells that were liquid-cultured for 11 days as the target cells. The results are shown below.

Control (absence of cell stimulatory factors): 96.7%

Positive control (presence of cell stimulatory factors): 98.1%

KS-13 (1 μg/mL): 97.5%

KS-13 (10 μg/mL): 97.6%

These results revealed that KS-13 does not induce cell death.

(2-5) Colony-Forming Cell Assay (Measurement of the Number of Hematopoietic Progenitor Cells)

Figure 6:
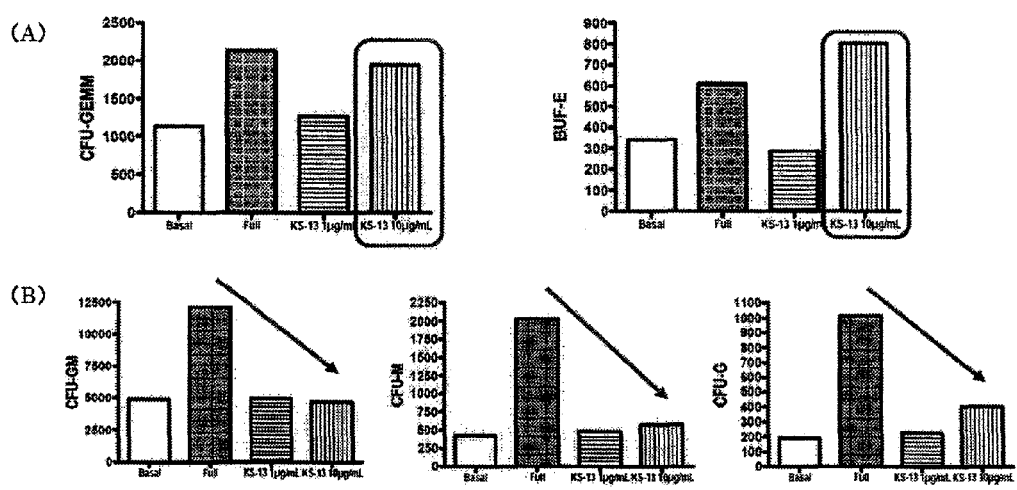
FIG. 6 shows the result obtained by performing colony-forming cell assay and counting the number of hematopoietic progenitor cells, after 11 days of culturing a human cord blood CD34(+) hematopoietic stem cell population in a medium (basal) containing cell stimulatory factors (50 ng/mL of SCF, 10 ng/mL of TPO, and 20 ng/mL of Flt3L), medium (full) containing a cell stimulatory factor mixture (50 ng/mL of SCF, 10 ng/mL of TPO, 20 ng/mL of Flt3L, 20 ng/mL of IL-6, and 20 ng/mL of sIL-6R), medium (KS-13 (1 μg/mL)) containing 1 μg/mL of KS-13, and medium (KS-13 (10 μg/mL)) containing 10 μg/mL of KS-13 (Experimental Example 2). The graph on the left in (A) shows the count of CFU-GEMM (colony-forming unit-granulocyte/erythrocyte/macrophage/megakaryocyte), the graph on the right in (A) shows the count of BFU-E (burst-forming unit-erythrocyte), the graph on the left in (B) shows the count of CFU-GM (colony-forming unit-granulocyte/macrophage), the graph in the middle in (B) shows the count of CFU-M (colony-forming unit-macrophage), and the graph on the right in (B) shows the count of CFU-G (colony-forming unit-granulocyte).

FIG. 6 shows the results obtained by measuring the number of colonies of various hematopoietic progenitor cells (CFU-GEMM (colony-forming unit-granulocyte/erythrocyte/macrophage/megakaryocyte), BFU-E (burst-forming unit-erythrocyte), CFU-GM (colony-forming unit-granulocyte/macrophage), CFU-M (colony-forming unit-macrophage), and CFU-G (colony-forming unit-granulocyte)) for each experimental system (control, positive control, KS-13 (1 μg/mL), and KS-13 (10 μg/mL)), using cells that were liquid-cultured for 11 days as the target cells.

As shown in FIG. 6, in the presence of cell stimulatory factors (positive control; indicated as "Full" in the figure), amplification of all of the progenitor cells (CFU-GEMM, BFU-E, CFU-GM, CFU-M, and CFU-G) was recognized and differential growth of human cord blood CD34(+) cells was observed, compared to the control (indicated as "Basal" in the figure). In contrast, in the case of KS-13 at a concentration of 10 μg/mL, CFU-GEMM, which is considered to be most similar to hematopoietic stem cells, was amplified about 2-fold in a manner dependent on the amount of KS-13, and BFU-E (i.e., relatively more differentiated and mature erythroid progenitor cells) was amplified approximately 2.5-fold (FIG. 6(A)), compared to the control (indicated as "Basal" in the figure). However, CFU-GM, CFU-G, and CFU-M, which are relatively more differentiated and mature myeloid progenitor cells, were not amplified (FIG. 6(B)). From these results, it became clear that KS-13 inhibits the process of maturation and differentiation of human cord blood CD34(+) cells into myeloid cells, and thereby amplifies mixed hematopoietic progenitor cells (CFU-GEMM) that can be differentiated into multiple lines of blood cells and amplifies erythroid progenitor cells (BFU-E) other than myeloid.

Experimental Example 3

Internalization of KS-13 in Bone-marrow Hematopoietic Cells (1) Flow Cytometry Analysis Mouse bone marrow cells were treated with biotin-labeled KS-13 and subsequently stained using markers of hematopoietic stem cells, such as CD45 antibody (CD45 conjugated with PE-Cy7: Biolegend), c-Kit antibody (c-Kit conjugated with APC: Biolegend), and Sca-1 antibody (Sca-1 conjugated with PE: Biolegend), and fluorescent-labeled streptavidin (streptavidin conjugated with FITC: Biolegend). Analysis was performed using flow cytometry.

FIGS. 7(A) and (B) show the results.

Figure 7:
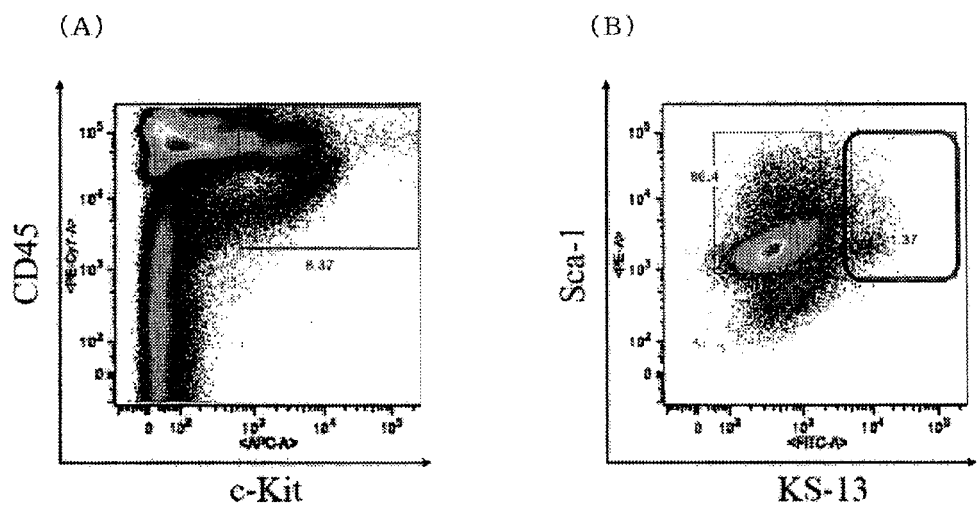
FIG. 7 shows the results obtained by treating mouse bone marrow cells with biotin-labeled KS-13, subsequently staining the cells with CD45 antibody (Biolegend), c-Kit antibody (Biolegend), and Sca-1 antibody (Biolegend), which are markers of hematopoietic stem cells, and with fluorescent-labeled streptavidin, and analyzing the cells using flow cytometry.

As shown in FIG. 7, it became clear that KS-13 is internalized into some of the CD45(+)c-Kit(+)Sca-1 (+) cells that reflect hematopoietic stem cells.

(2) Immunostaining Method

Frozen sections of the liver (i.e., an organ for hematopoietic stem cell amplification) of fetal mice of 12.5 days of gestational age were prepared and stained using biotin-labeled KS-13. Specifically, after washing with PBS(−), frozen sections were blocked (a procedure to suppress non-specific responses) with 1% BSA PBS(−) solution for 30 minutes and allowed to react with anti-mouse c-Kit antibody (R&D systems, AF1356) and biotin-labeled KS-13 at 4° C. overnight. After reaction, the reaction product was washed with PBS(−) and allowed to react with Anti-goat IgG conjugated with Alexa 488 (Invitrogen), streptavidin conjugated with Alexa 546 (Invitrogen), and TOTO-3 (Invitrogen) at room temperature for 30 minutes. After washing with PBS(−), a mounting medium (DAKO) was used to mount the reaction product, followed by observation using a confocal laser scanning microscope (Olympus FV-1000).

Figure 8:
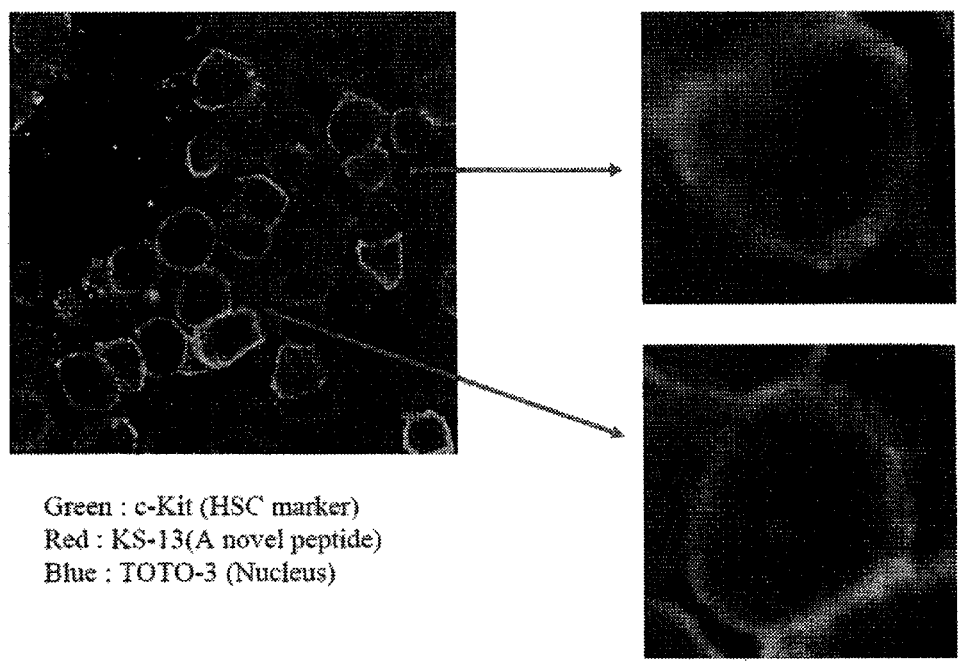
FIG. 8 shows the results obtained by preparing frozen section of the liver (i.e., an organ for hematopoietic stem cell amplification) of fetal mice (12.5 days of gestational), staining the sections using biotin-labeled KS-13, and observing the results using a confocal laser scanning microscope (Experimental Example 3). In the images, sites stained in green are c-Kit(+) hematopoietic stem cells, sites stained in red are cells having KS-13, and sites stained in blue are nuclei. The results show that KS-13 is internalized into c-Kit(+) hematopoietic stem cells by endocytosis and reaches into the nucleus.

FIG. 8 shows the results. As shown in FIG. 8, in hematopoietic stem cells, there are some cells that internalize KS-13 and others that do not. This corresponded to the results (FIG. 7) of the flow cytometry described in the above section (1). Further, the results suggested that KS-13 is internalized into hematopoietic stem cells and progenitor cells by endocytosis and reaches the membrane surface and into the nucleus.

Experimental Example 4

Analysis of KS-13-Binding Protein in Mouse

Biotin-labeled KS-13 was reacted with mouse fetal liver cells (12.5 days of gestational age) on ice for 1 hour, washed with PBS(−), and reacted with streptavidin microbeads (Miltenyi Biotec 130-048-102). Microbeads were assumed to be attached to cells that internalize KS-13 in this procedure. Next, this sample was passed through a MACS column (Miltenyi Biotec LS column) to trap cells that internalized KS-13 in the column. 1% triton (Wako Chemical) was passed through the column to disrupt the cell membrane. Subsequently, 6-8 M urea solution or 2.5 M glycine solution was passed through the column, and a series of proteins that bind to KS-13 was extracted. The extract was used to analyze proteins that bind to KS-13 by multidimensional protein identification technology (MudPIT).

Figure 9:
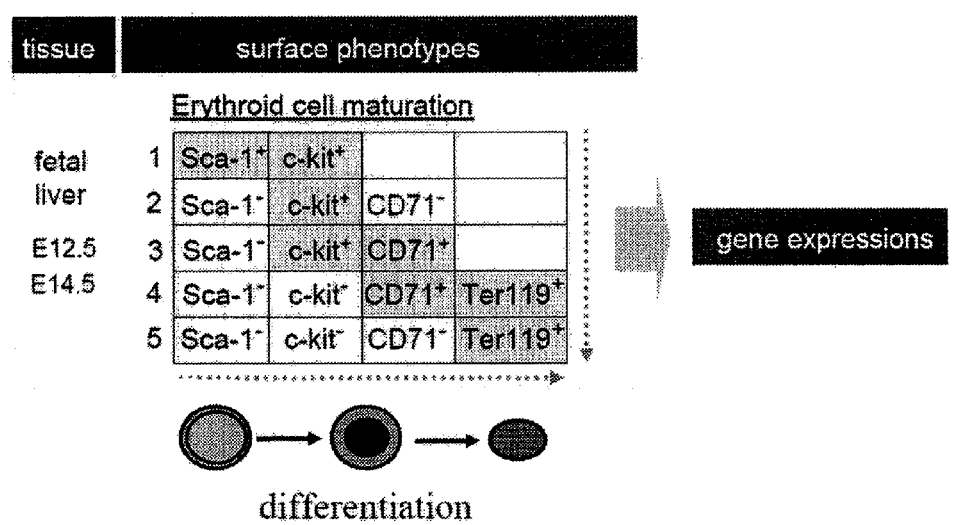
FIG. 9 shows patterns of protein expression on the cell surface in the process of differentiation and maturation of hematopoietic stem cells into erythrocytes.

As shown in FIG. 9, in the process of differentiation and maturation of mouse hematopoietic stem cells into erythrocytes, changes occur in proteins that are expressed on the cell surface ("Sca-1 (+)c-kit(+)"→"Sca-1 (−)c-kit(+) CD71(−)"→"Sca-1 (−)/c-kit(+)/CD71(+)"→"Sca-1 (−)/c-kit(−)/CD71(+)/Ter119(+)"→"Sca-1 (−)/c-kit(−)/CD71(−)/Ter119(+)"). Using the above combinations, these cell populations were purified and collected by flow cytometry, followed by mRNA extraction and cDNA synthesis. Next, primers of the genes identified from MudPIT data were designed, and changes in the gene expression in the process of differentiation and maturation of mouse hematopoietic stem cells into erythrocytes were examined using a real-time PCR method.

Figure 10:
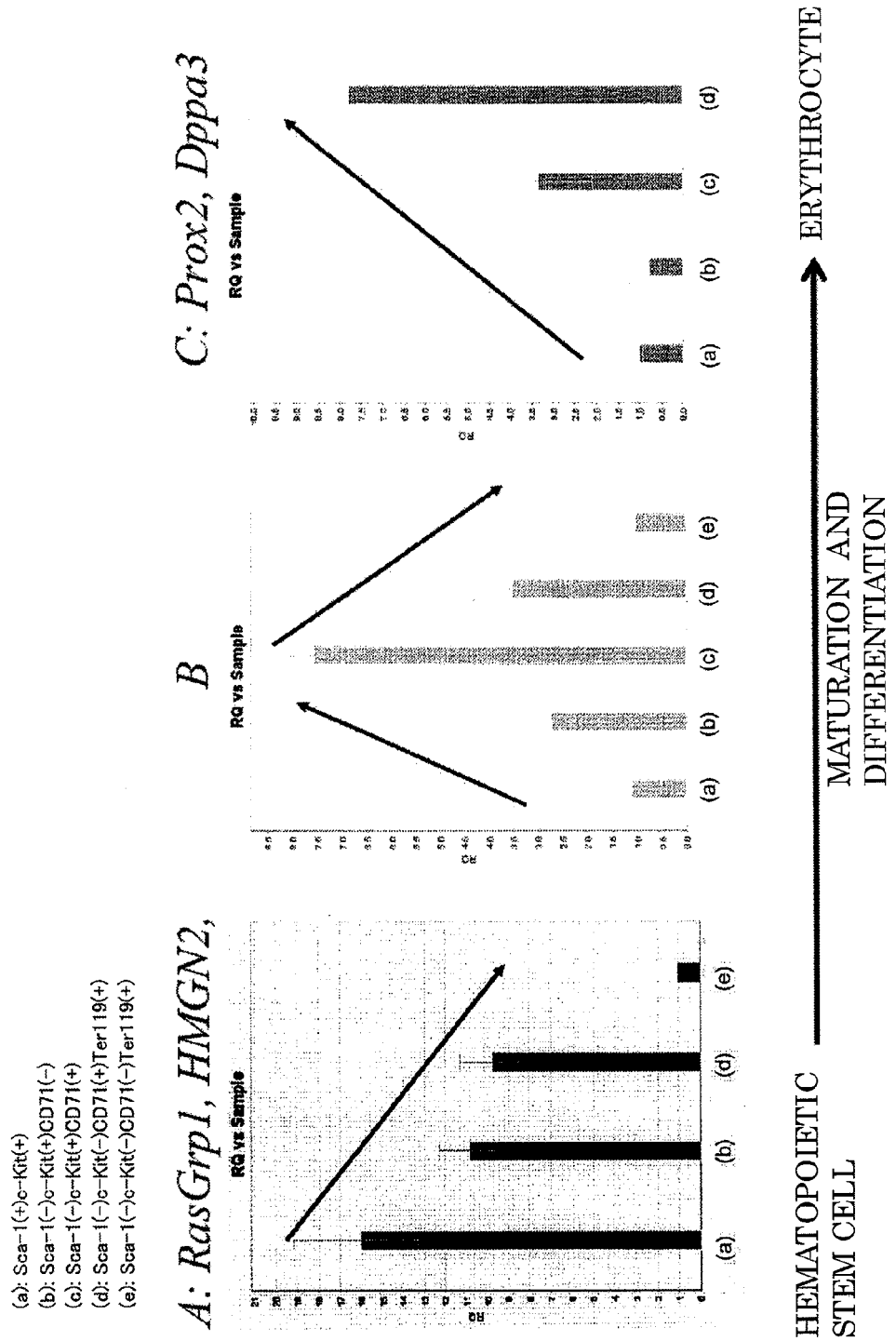
FIG. 10 shows the results obtained by using a real-time PCR method to examine changes in expression of genes identified by the MudPIT method in the process of differentiation and maturation of mouse hematopoietic stem cells into erythrocytes (Experimental Example 4). It is clear that there are three patterns, i.e., A, B, and C, in the gene expression in the process of differentiation and maturation of mouse hematopoietic stem cells into erythrocytes.

FIG. 10 shows the results.

As shown in FIG. 10, in the process of differentiation of hematopoietic stem cells into erythrocytes, certain gene expression patterns were identified. These gene expression patterns were able to be classified into the following categories: pattern A, in which gene expression decreases as hematopoietic stem cells are more differentiated into erythrocytes (this suggests that genes in this pattern are important for the maintenance of hematopoietic stem cells); pattern B, in which gene expression increases at the middle stage of differentiation of hematopoietic stem cells into erythrocytes (expression increases transiently to allow hematopoietic stem cells to be differentiated); and pattern C, in which gene expression increases as hematopoietic stem cells are more differentiated into erythrocytes (this suggests that genes in this pattern are important for differentiation of hematopoietic stem cells into erythrocytes). Examples of genes that fit these patterns include RasGrp1 and HMGN2 for pattern A, HDGF for pattern B, and Prox2 and Dppa3 for pattern C.

It became clear from the above results that the group of proteins that bind to KS-13 is involved in differentiation. The above results also clarified that KS-13 can be used not only for the amplification or production of tissue-specific stem cells or progenitor cells thereof but also for the identification of new differentiation-related factors. Further, an antibody against KS-13 can also be similarly used for the identification of differentiation-related factors.

Experimental Example 5

Phosphorylation of Akt and p53

Figure 11:
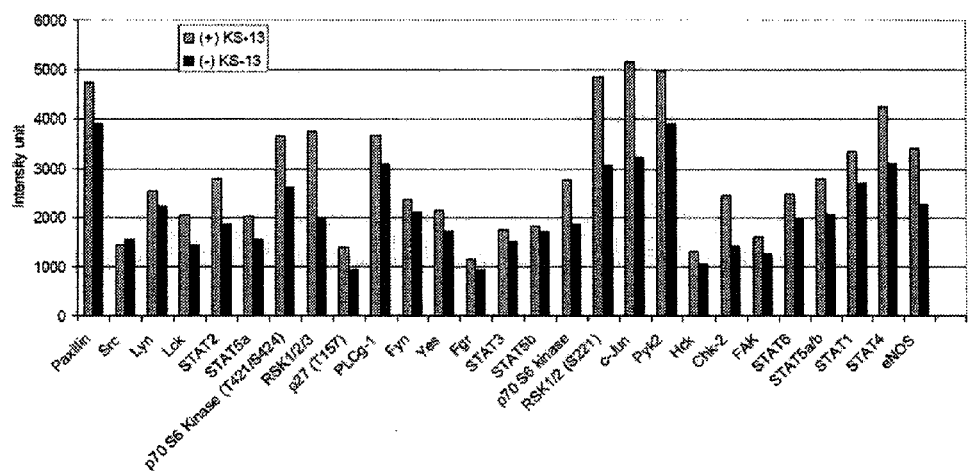
FIG. 11 shows the results obtained by culturing human cord blood CD34(+) cells in a KS-13-containing or KS-13-free medium for 2 days, subsequently extracting proteins, and measuring the presence or absence of phosphorylation using a Phospho-Kinase Array Kit, Human, Proteome Profiler (R&D Cat. No. ARY003) (Experimental Example 5).
Figure 11:
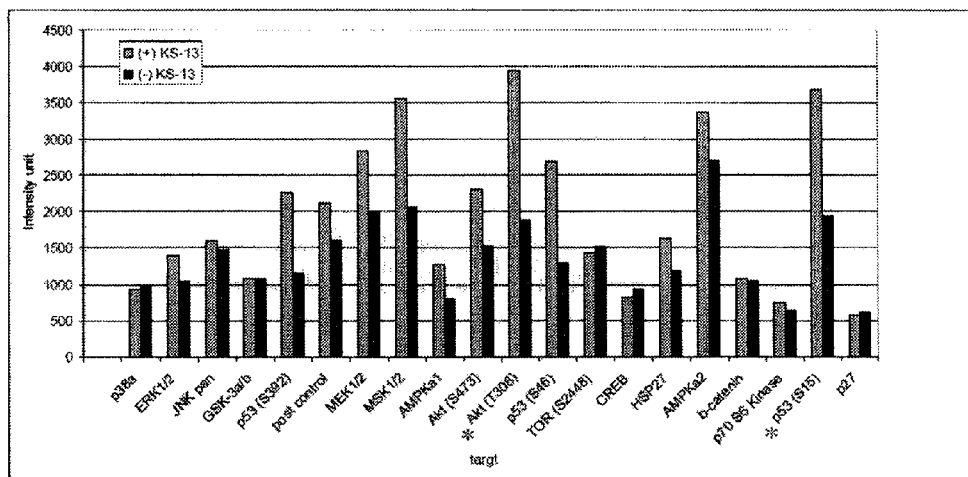

In order to examine what signaling pathway is activated by KS-13, first, human cord blood CD34(+) cells were cultured in a KS-13-containing medium (X-VIVO 10) for 2 days. Next, proteins were extracted using a Qproteome Mammalian Protein Prep Kit (Qiagen, Cat. No. 37901), and phosphorylation of various signaling pathways was examined using a Proteome Profiler Human Phospho-Kinase Array Kit (R&D Cat. No. ARY003). The results shown in FIG. 11 confirmed phosphorylation of the phosphorylation site (T308) of Akt and the phosphorylation site (S15) of p53. Based on these results, it became clear that KS-13 controls the signaling pathways of Akt and p53.

Experimental Example 6

Colony-Forming Fibroblasts (CFU-F) Assay

Mouse bone marrow cells ($2\times10^7$ cells) were cultured in a KS-13 (50 µg/mL)-containing liquid medium (MesenCult: STEMCELL Technologies) or in a KS-13-free liquid medium (same as above). Colony-forming fibroblasts (CFU-F) assay was performed to measure the number of CFU-F formation as an index of the number of mesenchymal stem cells.

Figure 12:
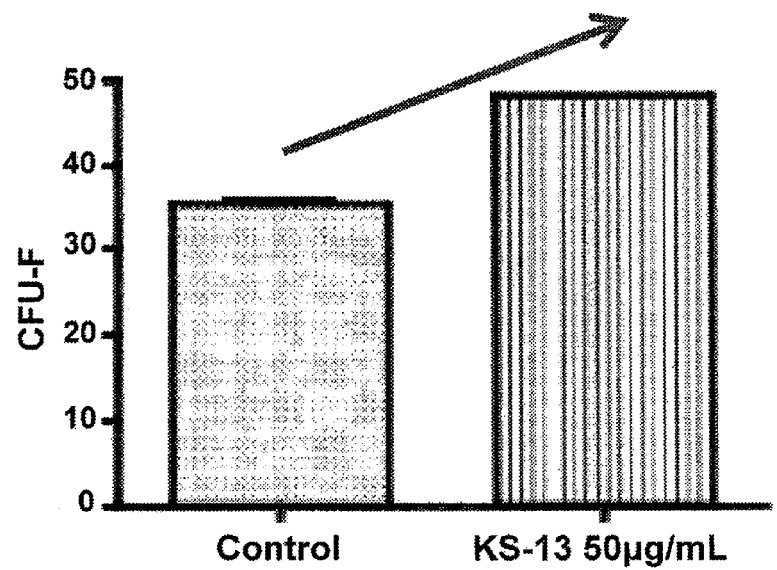
FIG. 12 shows the results obtained by liquid-culturing mouse bone marrow cells in the presence or absence of KS-13 (50 µg/mL) and measuring the number of CFU-F formation as an index of the number of mesenchymal stem cells by colony-forming fibroblasts (CFU-F) assay (Experimental Example 6).

FIG. 12 shows the results. As shown in FIG. 12, the number of CFU-F formation was 35.5 in a KS-13-free cultivation system (control), and the number of CFU-F formation was 48.0 in a KS-13 (50 µg/mL)-containing cultivation system. In the group to which KS-13 was added, the size of individual CFU-F tended to be small. This clarified that KS-13 amplifies mesenchymal stem cells 1.4-fold. Based on the above, it was suggested that KS-13 may be effective in the amplification of not only hematopoietic stem cells and hematopoietic progenitor cells but also mesenchymal stem cells and other tissue-specific stem cells (for example, tissue-specific stem cells such as neural stem cells and skin stem cells) via the factors identified by MudPIT and via the signaling pathways of Akt and p53.

Experimental Example 7

Figure 13:
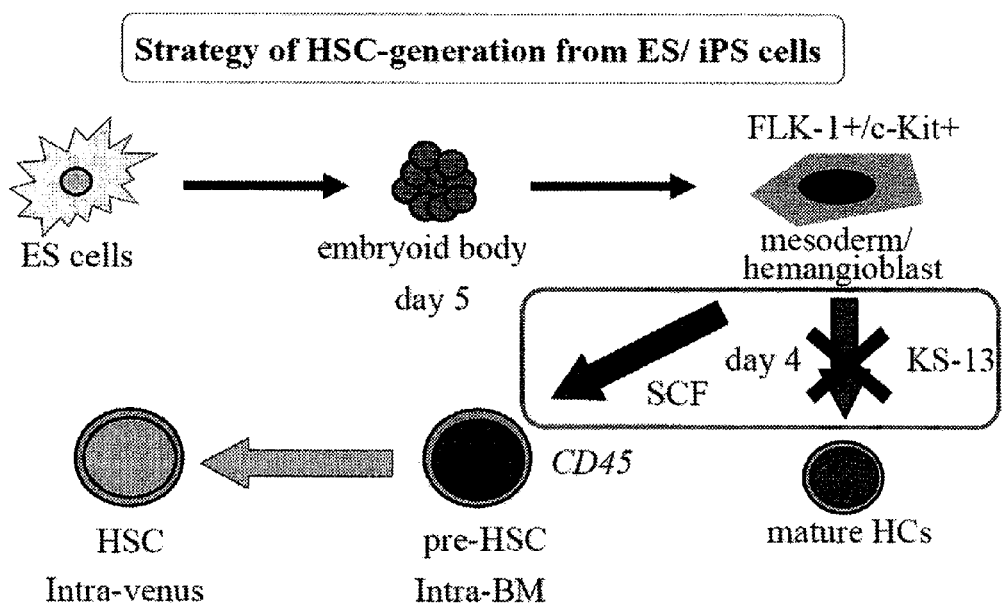
FIG. 13 shows a scheme for inducing hematopoietic stem cells and hematopoietic progenitor cells similar to hematopoietic stem cells from pluripotent stem cells in Experimental Example 7.

Induction of Hematopoietic Stem Cells and Similar Cells from Pluripotent Stem Cells In order to induce hematopoietic stem cells and hematopoietic progenitor cells similar to hematopoietic stem cells from pluripotent stem cells, embryoid body formation was induced from mouse embryonic stem cells, and then mesodermal cells were collected by flow cytometry. After culturing in the presence of SCF and KS-13, the gene expression and the hematopoietic potential were analyzed (FIG. 13).

Mouse embryonic stem cells (CCE) ($6\times10^4$ cells) were cultured in a culture solution described below for 5 days to form an embryoid body.

Composition of the Culture Solution:

15% FBS (fetal bovine serum), 2 mM L-glutamine (Sigma-Aldrich) 0.0026% (vol/vol) monothioglycerol (MTG, Wako Pure Chemical Industries, Osaka, Japan), 50 mg/mL L-ascorbic acid (Wako Pure Chemical Industries), 10 U/mL penicillin, and 10 mg/mL streptomycin (Sigma-Aldrich).

After pipetting, the embryoid body was incubated in a cell dissociation buffer (Life Technologies, Carlsbad, Calif.) at 37° C. for 30 minutes to dissociate the cell mass into single cells, followed by reaction with Alexa Fluor (registered trademark) 647-conjugated anti-CD324 (E-cadherin) Ab (eBioscience, San Diego, Calif.), Pacific Blue (trademark) anti-mouse Flk-1 (VEGFR2) Ab (BioLegend, San Diego, Calif.), and PE-Cy7-conjugated anti-mouse c-Kit (CD117) Ab (eBioscience) on ice for 30 minutes. After washing with PBS(−), CD324(−)Flk-1 (+)c-Kit(+) cells were collected by flow cytometry.

Next, the collected CD324(−)Flk-1 (+)c-Kit(+) cells were cultured in the presence and absence of 50 ng/ml, of rm SCF (Peprotech) and 100 μg/ml, of KS-13 for several days, and the expressions of CD45, Runx-1, and HoxB4 genes were examined by real-time PCR. A TaqMan probe (Life Technologies) was used for each gene, and the analysis was performed using StepOnePlus (Life Technologies).

Figure 14:
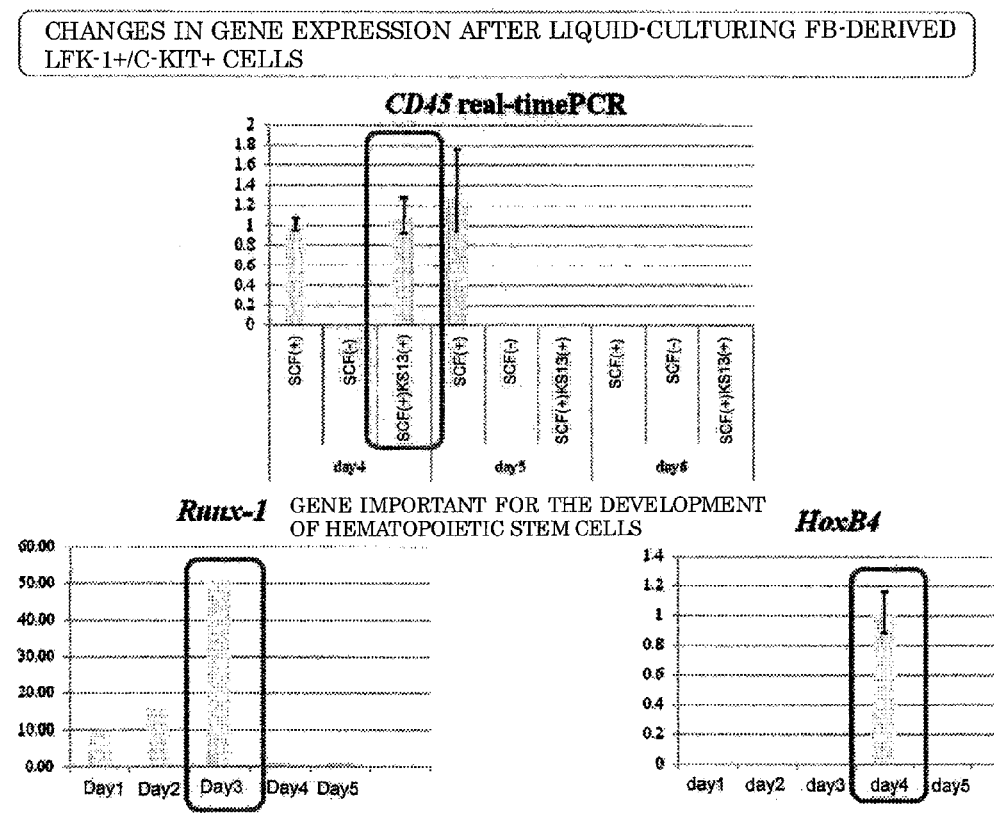
FIG. 14 shows the results obtained by culturing mesodermal cells (CD324(−)Flk-1 (+)c-Kit(+) cells) induced from mouse embryonic stem cells via embryoid body formation in the presence or absence of 50 ng/mL of SCF and 100 µg/mL of KS-13 for several days, and examining the expressions of CD45 gene, Runx-1 gene, and HoxB4 gene by real-time PCR (Experimental Example 7).

FIG. 14 shows the results.

As shown in FIG. 14, CD45 gene expression as a marker of hematopoietic cells was observed in a SCF monoculture and SCF/KS-13 co-culture at day 4 of culturing, and in a SCF monoculture at day 5 of culturing. However, CD45 gene expression was not observed in a SCF/KS-13 co-culture at day 5 of culturing. In the SCF/KS-13 co-culture group, expressions of Runx-1 and HoxB4 genes were examined over time. As a result, the expression of Runx-1 reached its peak at day 3 of culturing, and the expression of HoxB4 gene reached its peak at day 4 of culturing. CD45 gene is an early marker of hematopoietic cell development, and the fraction of CD45(+) may have developed hematopoietic stem cells. The expression of Runx-1 gene increases immediately before the development of hematopoietic stem cells. Further, although hematopoietic stem cells are induced when HoxB4 gene is introduced into ES cells, prolonged overexpression causes leukemia.

Based on the above results, it was assumed that at day 4 of culturing with SCF and KS-13, hematopoietic stem cells and cells similar to hematopoietic stem cells were derived from CD324(−)Flk-1(+)c-Kit(+) cells, which are mesodermal cells induced from mouse embryonic stem cells via embryoid body formation.

Figure 15:
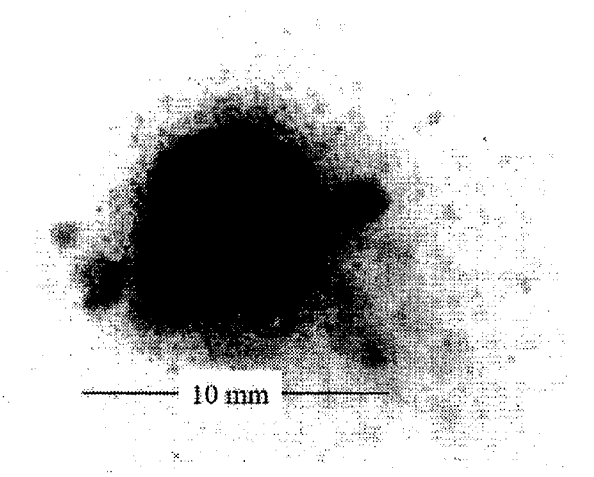
FIG. 15 shows an image obtained by culturing mesodermal cells (CD324(−)Flk-1 (+)c-Kit(+) cells) induced from mouse embryonic stem cells via embryoid body formation in a semi-solid medium containing cell stimulatory factors (50 ng/mL of rm SCF, 10 ng/mL of rm IL-3, 10 ng/mL of rh IL-6, and 3 U/mL rh EPO) for 1 month, and observing the resulting cells (Experimental Example 7).

Consequently, these cells were cultured in a semisolid medium (Methocult M3434; produced by STEMCELL Technologies) containing cell stimulatory factors (50 ng/mL of rm SCF, 10 ng/mL of rm IL-3, 10 ng/mL of rh IL-6, and 3 U/mL of rh EPO). A month later, high-proliferative-potential colony-forming cells (HPP-CFC) (i.e., cells having a diameter of over 10 mm, which are similar to hematopoietic stem cells) were observed (FIG. 15).

From the above results, it became clear that KS-13 has an effect of inducing cells similar to hematopoietic stem cells from mouse pluripotent stem cells.

Because HPP—CFC was induced under the above cultivation conditions, ES cells for use were changed from CCE strain to BRCS strain derived from an inbred mouse strain C57BL6, which is suitable for transplantation experiments, and hematopoietic stem cell ability was examined.

Cells for transplantation were prepared using a similar procedure as used for CCE strain. Ly-5.1 mice that do not reject transplants of C57BL6-derived cells were used as recipients. These recipient mice were irradiated with a 7.5 gray radiation, and BRC cell line-derived cells and 1×10$^5$ of Ly-5.1 mouse bone marrow cells for rescue were mixed. Then, cells were transplanted via bone marrow and the tail vein.

Figure 16:
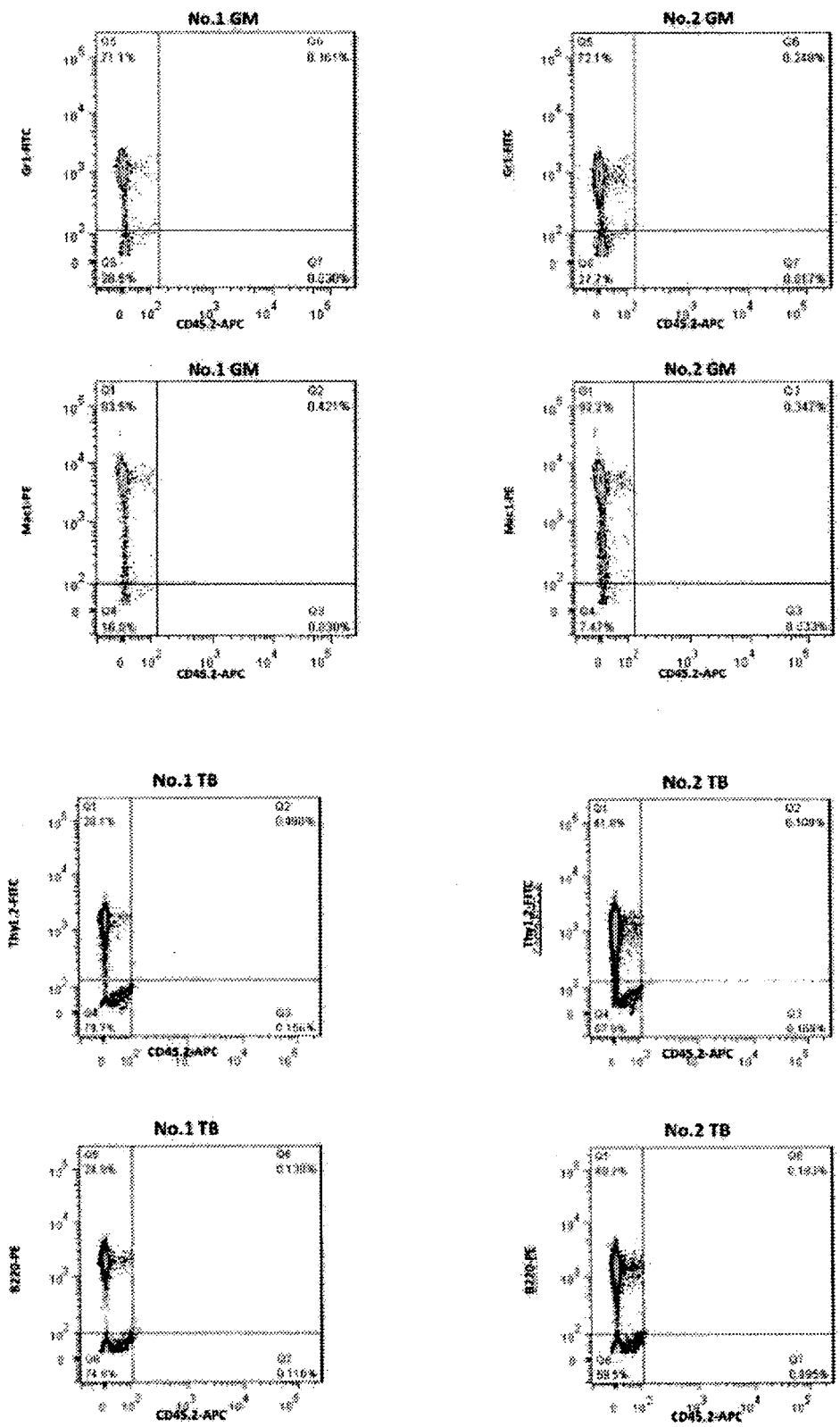
FIG. 16 shows 3D plot images showing the results obtained by transplanting about 2,000 cells into bone marrow of two recipient mice (No. 1 and No. 2) and evaluating bone marrow reconstruction potential (which indicates hematopoietic stem cell activity) using flow cytometry, 3 to 4 months after the transplantation (Experimental Example 7).
Figure 17:
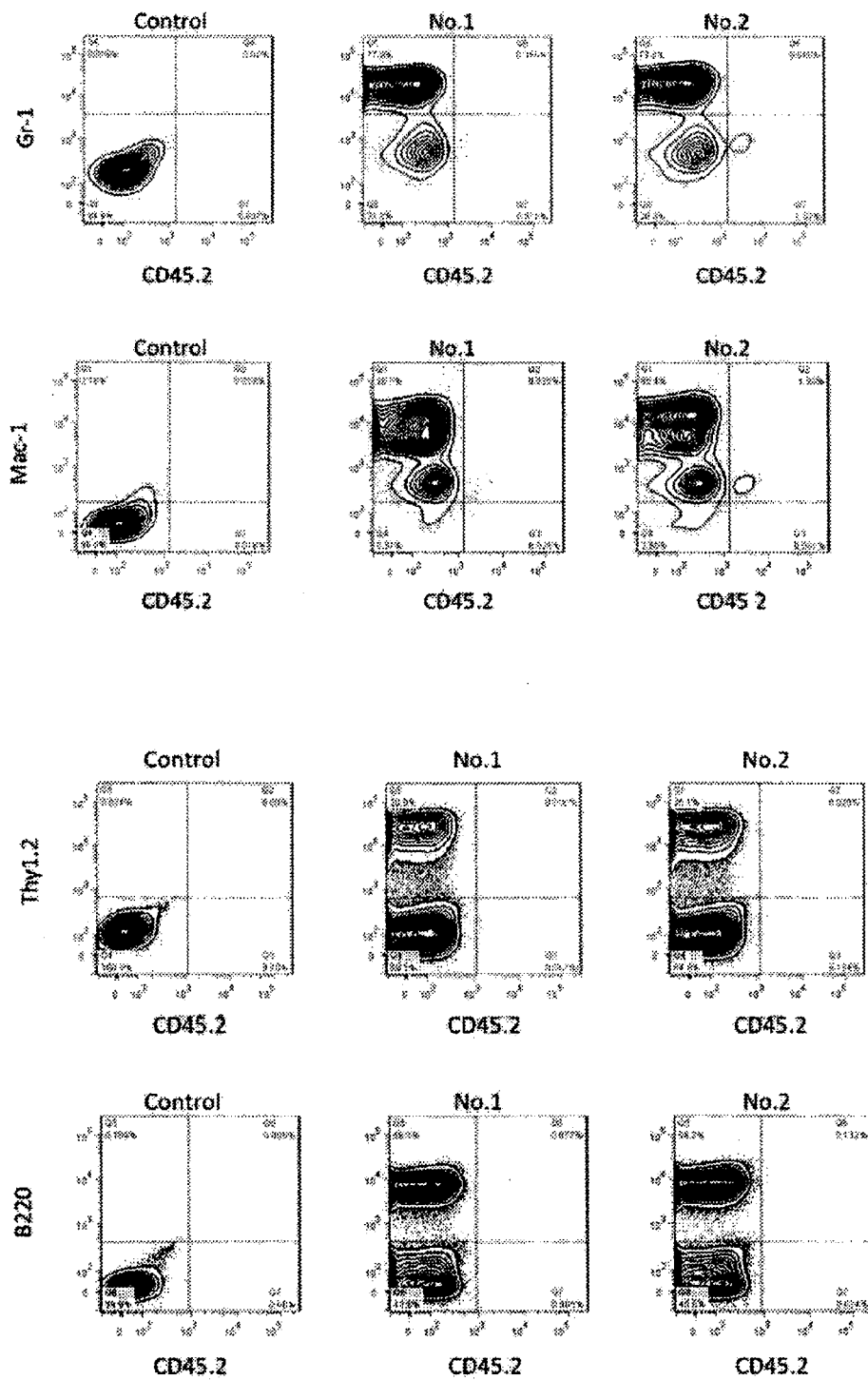
FIG. 17 shows 3D plot images showing the results obtained by transplanting about 20,000 cells into the tail vein of two recipient mice (No. 1 and No. 2) and evaluating bone marrow reconstruction potential (which indicates hematopoietic stem cell activity) using flow cytometry, 2 months after the transplantation.
Figure 18:
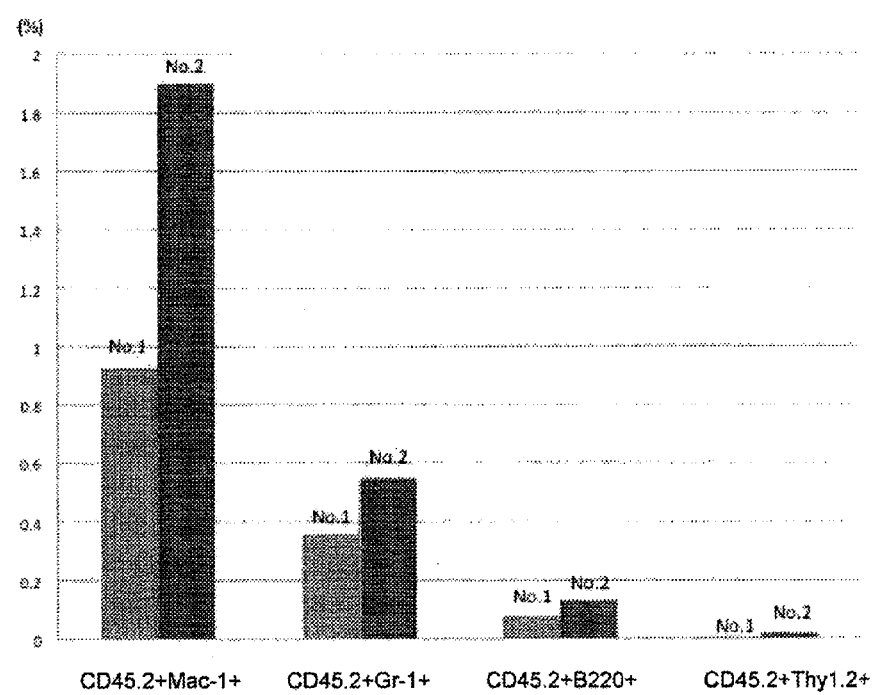
FIG. 18 shows the results obtained by transplanting about 20,000 cells into the tail vein of two recipient mice (No. 1 and No. 2) and evaluating bone marrow reconstruction potential (which indicates hematopoietic stem cell activity) using flow cytometry 2 months after the transplantation. The presence of cells (CD45.2(+)Gr-1(+):CD45.2(+)Mac-1(+):CD45.2(+)Thy1.2(+):CD45.2(+)B220(+)) that indicate bone marrow reconstruction was identified in both mice.

FIGS. 16, 17, and 18 show the results.

As shown in FIG. 16, about 2,000 cells were transplanted into bone marrow of two recipient mice. 3 to 4 months later, bone marrow reconstruction potential, which indicates hematopoietic stem cell ability, was evaluated using flow cytometry. Despite the fact that chimerism levels were low, the reconstruction of bone marrow was recognized in the two mice that received transplants. (In control, CD45.2(+)Gr-1 (+): 0.041%; CD45.2(+)Mac-1 (+): 0.082%; CD45.2(+)Thy1.2(+): 0.085%; and CD45.2 (+)B220(+): 0.092%. In No. 1, CD45.2(+)Gr-1 (+): 0.361%; CD45.2(+)Mac-1 (+): 0.421%; CD45.2(+)Thy1.2(+): 0.090%; and CD45.2(+)B220 (+): 0.130%. In No. 2, CD45.2(+)Gr-1 (+): 0.248%; CD45.2 (+)Mac-1 (+): 0.347%; CD45.2(+)Thy1.2(+): 0.109%; and CD45.2(+)B220(+): 0.183%.)

As shown in FIGS. 17 and 18, about 20,000 cells were transplanted into the tail vein of two recipient mice. 2 months later, bone marrow reconstruction potential, which indicates hematopoietic stem cell ability, was evaluated using flow cytometry. The reconstruction of bone marrow was recognized in the two mice that received transplants. (In control, CD45.2(+)Gr-1(+): 0%; CD45.2(+)Mac-1 (+): 0.018%; CD45.2(+)Thy1.2(+): 0%; and CD45.2(+)B220(+): 0.005%. In No. 1, CD45.2(+)Gr-1 (+): 0.356%; CD45.2(+)Mac-1 (+): 0.925%; CD45.2(+)Thy1.2(+): 0.006%; and CD45.2(+)B220 (+): 0.077%. In No. 2, CD45.2(+)Gr-1 (+): 0.548%; CD45.2 (+)Mac-1 (+): 1.90%; CD45.2(+)Thy1.2(+): 0.020%; and CD45.2(+)B220(+): 0.132%.)

From the above results, it became clear that KS-13 is effective in the induction of hematopoietic stem cells and similar cells thereof from pluripotent stem cells.

Experimental Example 8

Amplification of Mouse Hematopoietic Stem Cells by the Addition of KS-13

Hematopoietic stem cells (CD45(+)c-Kit(+)Sca-1 (+)) were purified and collected from the mouse fetal liver (12.5 days of gestational age) using the flow cytometry method, and in vitro amplification was attempted by culturing the cells in a KS-13 (30 μg/mL)-containing liquid medium (serum-free synthetic medium for lymphocytes (X-VIVO 10: Takara) to which 50 ng/mL of SCF and 50 ng/mL of TPO were separately added). As a control test (control), a KS-13-free liquid medium (serum-free synthetic medium for lymphocytes (X-VIVO 10: Takara) to which 50 ng/mL of SCF and 50 ng/mL of TPO were separately added) was used. At day 4 of culturing, in vitro amplified cells (about 10,000 cells) and Ly-5.1 mouse bone marrow cells (1×10$^5$) for rescue were mixed, and the mixed cells were transplanted to the recipient Ly-5.1 mice irradiated with radiation via bone marrow and the tail vein (in vitro amplification group: 3 mice; control: 2 mice). 5 months after transplantation, bone marrow reconstruction potential, which indicates hematopoietic stem cell activity, was evaluated using flow cytometry.

Figure 19:
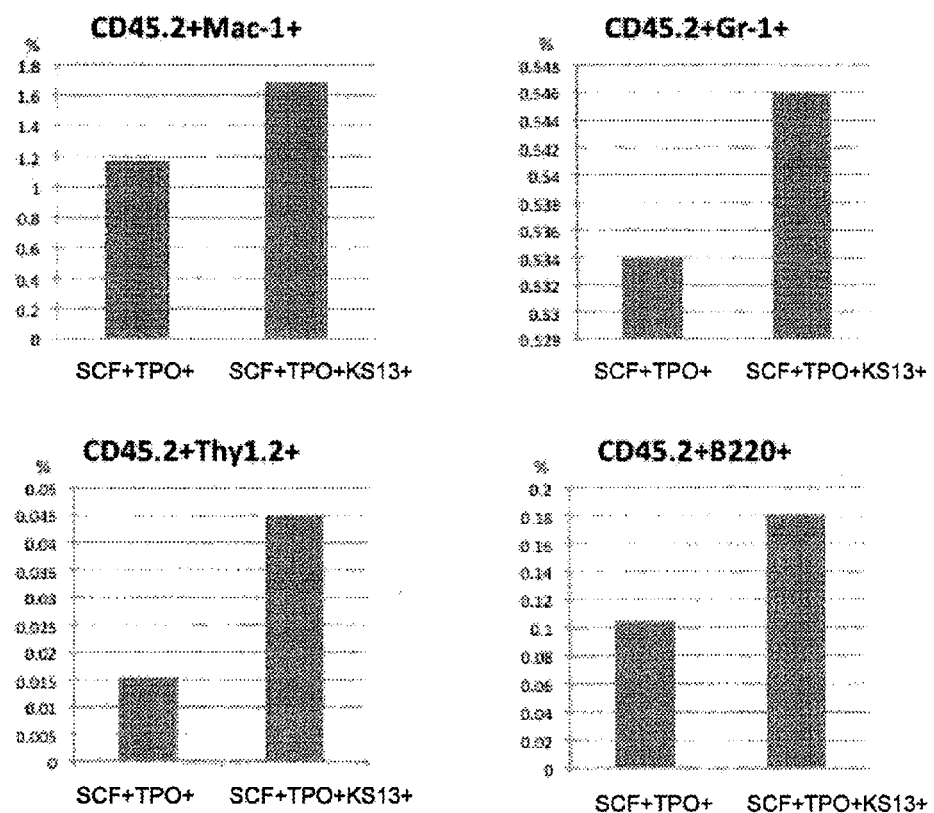
FIG. 19 shows the results obtained by culturing hematopoietic stem cells (CD45(+)c-Kit(+)Sca-1(+)) in the presence of KS-13 (30 µg/mL) for in vitro amplification and evaluating bone marrow reconstruction potential of the resulting cellular aggregates (Experimental Example 8).

As shown in FIG. 19, reconstructed bone marrow showed higher chimerism in all blood cell lines, compared to the control. (In the control group, CD45.2(+)Gr-1 (+): 0.534%; CD45.2(+)Mac-1(+): 1.1725%; CD45.2(+)Thy1.2(+): 0.0155%; and CD45.2(+)B220(+): 0.1045%. In the in vitro amplification group, CD45.2(+)Gr-1 (+): 0.546%; CD45.2 (+)Mac-1 (+): 1.69%; CD45.2(+)Thy1.2(+): 0.045%; and CD45.2(+)B220(+): 0.181%.)

This suggested that KS-13 is effective in in vitro amplification of hematopoietic stem cells.

Experimental Example 9

Effect of KS-13 Modification

Myristoylated KS-13 (30 μg/mL) in which the N-terminal of KS-13 (SEQ ID NO: 1) is myristoylated and control peptide (NQVSIGCPCDGKK: SEQ ID NO: 22) (30 µg/mL) were added to a semisolid medium (Methocult M3434 produced by STEMCELL Technologies) containing cell stimulatory factors (50 ng/mL of rm SCF, 10 ng/mL of rm IL-3, 10 ng/mL of rh IL-6, and 3 U/mL of rh EPO) (rm: recombinant form; rh: recombinant human form) to culture mouse fetal liver hematopoietic stem cells (CD45(+)$_c$— Kit(+)Sca-1(+)) (1,000 cells/dish) therein. Then, hematopoietic colony-forming cell assay was performed to evaluate the hematopoietic potential of the cells.

Figure 20:
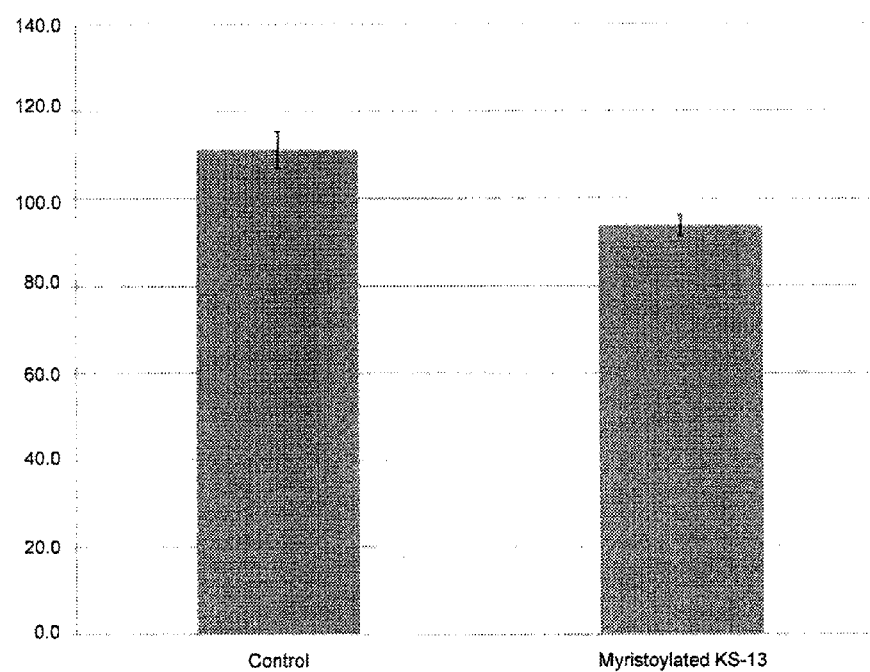
FIG. 20 shows the results obtained by culturing mouse fetal liver hematopoietic stem cells (CD45(+)c-Kit(+)Sca-1 (+)) in the presence of control peptide or myristoylated KS-13 in which the N-terminal of KS-13 (SEQ ID NO: 1) is myristoylated, and by performing hematopoietic colony-forming cell assay to examine the hematopoietic potential of the cells (Experimental Example 9). The vertical axis shows the number of colonies.

FIG. 20 shows the results obtained by measuring the number of colonies formed after culturing for 12 days. According to a comparison between control peptide (number of colonies: 111.1) and myristoylated KS-13 (number of colonies: 93.9), myristoylated KS-13 inhibited colony formation more than the control.

The above suggested that myristoylated KS-13 may inhibit differential growth of hematopoietic stem cells (CD45(+)c-Kit(+)Sca-1 (+)) in the presence of cell stimulatory factors.

Experimental Example 10

Analysis of KS-13-Binding Protein in Human

Biotin-labeled KS-13 was reacted with human cord blood CD34(+) cells on ice for 1 hour, washed with PBS (-), and reacted with streptavidin-microbeads (Miltenyi Biotec 130-048-102). Microbeads were assumed to be attached to cells that internalize KS-13 in this procedure. Next, this sample was passed through a MACS column (Miltenyi Biotec LS column) to trap cells that internalized KS-13 in the column. 1% triton (Wako Chemical) was passed through the column to disrupt the cell membrane. Subsequently, 6-8 M urea solution or 2.5 M glycine solution was passed through the column, and a series of proteins that bind to KS-13 was extracted. The extract was used to analyze proteins that bind to KS-13 by multidimensional protein identification technology (MudPIT).

The top five proteins with a high emPAI value that reflects protein abundance are listed for each extraction method.

Urea Extraction 0.58: Uncharacterized protein C20orf54. 0.47: Ig lambda chain V-I region HA. 0.47: Protein CGI-301. 0.47: Protein transport protein Sec61 subunit beta. 0.27: D NA-binding protein A.

Glycine Extraction 0.58: Small nuclear ribonucleoprotein G-like protein. 0.39: Host cell factor C1 regulator 1. 0.39: Keratin, type I cytoskeletal 16. 0.28: Keratin, type I cytoskeletal 14. 0.28: Tropomyosin beta chain.

As in the case of the analysis of mice, factors such as HDGF and ubiquitin-associated factors, which control differentiation and growth, were also identified, although their emPAI values are not high.

Based on the above, it became clear that KS-13 can also be used in the identification of novel differentiation-associated factors in human.

Sequence Listing Free Text

SEQ ID NOs: 13 to 21 represent amino acid sequences of peptides designed from the amino acid sequences of the ectodomain from the cell membrane of hepatoblasts.

Sequence Listing

The invention claimed is:

1. A peptide set forth in (A) or (B) below:
   (A) an artificial peptide consisting of any one of SEQ ID NOs: 1 and 3 to 10; and
   (B) a peptide consisting of any one of SEQ ID NOs: 1 and 3 to 10, wherein:
   the C terminus is an amide ($-CONH_2$), or an ester ($-COOR$), wherein the group represented by R in the ester is an alkyl group containing 1 to 6 carbon atoms, a cycloalkyl group containing 3 to 8 carbon atoms, an aryl group containing 6 to 12 carbon atoms, a phenyl-$C_{1-2}$ alkyl group, a $C_{7-14}$ aralkyl group, or a pivaloyloxymethyl group; or
   a carboxy group or carboxylate at a position other than the C terminus of the peptide is amidated or esterified; or
   the amino group of the N-terminal amino acid residue is protected by a protecting group that is a $C_{1-6}$ acyl group, or is modified with a $C_{8-18}$ saturated fatty acid; or
   a substituent that is $-OH$, $-SH$, an amino group, or an imidazole group, on an amino acid side chain in the peptide is protected by a $C_{1-6}$ acyl group; or
   the peptide has a sugar chain bound thereto; or
   the peptide has an imidazolyl group or a SH group that is alkylated, aralkylated, or acylated.

2. A composition comprising at least one of the peptides set forth in claim 1 or a pharmaceutically acceptable salt or solvate thereof as an active ingredient.

3. The composition according to claim 2, the composition being adapted for a hematopoietic stem cell or hematopoietic progenitor cell differentiation inhibitor.

4. The composition according to claim 2, the composition being adapted for a. mesenchymal stem cell amplification promoter.

5. The compostion according to claim 2, the composition being adapted for a hemiatopoietic stem cell inducer.

* * * * *

```
SEQUENCE LISTING

<160> NUMBER OF SEQ ID NOS: 22

<210> SEQ ID NO 1
<211> LENGTH: 13
<212> TYPE: PRT
<213> ORGANISM: Homo sapiens

<400> SEQUENCE: 1

Cys Gln Lys Lys Asp Gly Pro Cys Val Ile Asn Gly Ser
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Peptide shown as "{(Cys XXa XXb)n XXc XXd}m Gly
      Pro Cys XXe XXf Asn Gly Ser" in a specification of the present
      application.
<220> FEATURE:
<221> NAME/KEY: VARIANT
<222> LOCATION: (2)..(2)
<223> OTHER INFORMATION: Gln or His
<220> FEATURE:
<221> NAME/KEY: VARIANT
<222> LOCATION: (3)..(3)
<223> OTHER INFORMATION: His, Lys, Glu, or Leu
<220> FEATURE:
<221> NAME/KEY: VARIANT
<222> LOCATION: (4)..(4)
<223> OTHER INFORMATION: Lys or Met
<220> FEATURE:
<221> NAME/KEY: VARIANT
<222> LOCATION: (5)..(5)
<223> OTHER INFORMATION: Ala, Asp, Glu or Gln
```

```
<220> FEATURE:
<221> NAME/KEY: VARIANT
<222> LOCATION: (9)..(9)
<223> OTHER INFORMATION: Val, Ala or Ile
<220> FEATURE:
<221> NAME/KEY: VARIANT
<222> LOCATION: (10)..(10)
<223> OTHER INFORMATION: Ile, Met or Val

<400> SEQUENCE: 2

Cys Xaa Xaa Xaa Xaa Gly Pro Cys Xaa Xaa Asn Gly Ser
1               5                  10

<210> SEQ ID NO 3
<211> LENGTH: 13
<212> TYPE: PRT
<213> ORGANISM: Mus musculus

<400> SEQUENCE: 3

Cys Gln His Lys Ala Gly Pro Cys Val Ile Asn Gly Ser
1               5                  10

<210> SEQ ID NO 4
<211> LENGTH: 13
<212> TYPE: PRT
<213> ORGANISM: Sus scrofa

<400> SEQUENCE: 4

Cys Gln Lys Lys Asp Gly Pro Cys Val Met Asn Gly Ser
1               5                  10

<210> SEQ ID NO 5
<211> LENGTH: 13
<212> TYPE: PRT
<213> ORGANISM: Equus caballus

<400> SEQUENCE: 5

Cys Gln Lys Lys Asp Gly Pro Cys Ala Ile Asn Gly Ser
1               5                  10

<210> SEQ ID NO 6
<211> LENGTH: 13
<212> TYPE: PRT
<213> ORGANISM: Capra hircus

<400> SEQUENCE: 6

Cys Gln Glu Met Asp Gly Pro Cys Val Val Asn Gly Ser
1               5                  10

<210> SEQ ID NO 7
<211> LENGTH: 13
<212> TYPE: PRT
<213> ORGANISM: Macropus eugenii

<400> SEQUENCE: 7

Cys His Leu Lys Glu Gly Pro Cys Val Ile Asn Gly Ser
1               5                  10

<210> SEQ ID NO 8
<211> LENGTH: 10
<212> TYPE: PRT
<213> ORGANISM: Monodelphis domestica

<400> SEQUENCE: 8

Lys Glu Gly Pro Cys Val Ile Asn Gly Ser
1               5                  10
```

```
<210> SEQ ID NO 9
<211> LENGTH: 13
<212> TYPE: PRT
<213> ORGANISM: Taeniopygia guttata

<400> SEQUENCE: 9

Cys His Leu Lys Gln Gly Pro Cys Ile Ile Asn Gly Ser
1               5                   10

<210> SEQ ID NO 10
<211> LENGTH: 8
<212> TYPE: PRT
<213> ORGANISM: Ornithorhynchus anatinus

<400> SEQUENCE: 10

Gly Pro Cys Ile Ile Asn Gly Ser
1               5

<210> SEQ ID NO 11
<211> LENGTH: 383
<212> TYPE: PRT
<213> ORGANISM: Homo sapiens

<400> SEQUENCE: 11

Met Thr Ala Thr Glu Ala Leu Leu Arg Val Leu Leu Leu Leu Leu Ala
1               5                   10                  15

Phe Gly His Ser Thr Tyr Gly Ala Glu Cys Phe Pro Ala Cys Asn Pro
                20                  25                  30

Gln Asn Gly Phe Cys Glu Asp Asp Asn Val Cys Arg Cys Gln Pro Gly
            35                  40                  45

Trp Gln Gly Pro Leu Cys Asp Gln Cys Val Thr Ser Pro Gly Cys Leu
    50                  55                  60

His Gly Leu Cys Gly Glu Pro Gly Gln Cys Ile Cys Thr Asp Gly Trp
65                  70                  75                  80

Asp Gly Glu Leu Cys Asp Arg Asp Val Arg Ala Cys Ser Ser Ala Pro
                85                  90                  95

Cys Ala Asn Asn Gly Thr Cys Val Ser Leu Asp Asp Gly Leu Tyr Glu
            100                 105                 110

Cys Ser Cys Ala Pro Gly Tyr Ser Gly Lys Asp Cys Gln Lys Lys Asp
        115                 120                 125

Gly Pro Cys Val Ile Asn Gly Ser Pro Cys Gln His Gly Gly Thr Cys
    130                 135                 140

Val Asp Asp Glu Gly Arg Ala Ser His Ala Ser Cys Leu Cys Pro Pro
145                 150                 155                 160

Gly Phe Ser Gly Asn Phe Cys Glu Ile Val Ala Asn Ser Cys Thr Pro
                165                 170                 175

Asn Pro Cys Glu Asn Asp Gly Val Cys Thr Asp Ile Gly Gly Asp Phe
            180                 185                 190

Arg Cys Arg Cys Pro Ala Gly Phe Ile Asp Lys Thr Cys Ser Arg Pro
        195                 200                 205

Val Thr Asn Cys Ala Ser Ser Pro Cys Gln Asn Gly Gly Thr Cys Leu
    210                 215                 220

Gln His Thr Gln Val Ser Tyr Glu Cys Leu Cys Lys Pro Glu Phe Thr
225                 230                 235                 240

Gly Leu Thr Cys Val Lys Lys Arg Ala Leu Ser Pro Gln Gln Val Thr
                245                 250                 255

Arg Leu Pro Asn Gly Tyr Gly Leu Ala Tyr Arg Leu Thr Pro Gly Val
            260                 265                 270
```

-continued

```
His Glu Leu Pro Val Gln Gln Pro Glu His Arg Ile Leu Lys Val Ser
            275                 280                 285

Met Lys Glu Leu Asn Lys Lys Thr Pro Leu Leu Thr Glu Gly Gln Ala
        290                 295                 300

Ile Cys Phe Thr Ile Leu Gly Val Leu Thr Ser Leu Val Val Leu Gly
305                 310                 315                 320

Thr Val Gly Ile Val Phe Leu Asn Lys Cys Glu Thr Trp Val Ser Asn
                325                 330                 335

Leu Arg Tyr Asn His Met Leu Arg Lys Lys Asn Leu Leu Leu Gln
            340                 345                 350

Tyr Asn Ser Gly Glu Asp Leu Ala Val Asn Ile Ile Phe Pro Glu Lys
        355                 360                 365

Ile Asp Met Thr Thr Phe Ser Lys Glu Ala Gly Asp Glu Glu Ile
    370                 375                 380

<210> SEQ ID NO 12
<211> LENGTH: 385
<212> TYPE: PRT
<213> ORGANISM: Mus musculus

<400> SEQUENCE: 12

Met Ile Ala Thr Gly Ala Leu Leu Arg Val Leu Leu Leu Leu Leu Ala
1               5                   10                  15

Phe Gly His Ser Thr Tyr Gly Ala Glu Cys Asp Pro Cys Asp Pro
                20                  25                  30

Gln Tyr Gly Phe Cys Glu Ala Asp Asn Val Cys Arg Cys His Val Gly
            35                  40                  45

Trp Glu Gly Pro Leu Cys Asp Lys Cys Val Thr Ala Pro Gly Cys Val
        50                  55                  60

Asn Gly Val Cys Lys Glu Pro Trp Gln Cys Ile Cys Lys Asp Gly Trp
65                  70                  75                  80

Asp Gly Lys Phe Cys Glu Ile Asp Val Arg Ala Cys Thr Ser Thr Pro
                85                  90                  95

Cys Ala Asn Asn Gly Thr Cys Val Asp Leu Glu Lys Gly Gln Tyr Glu
            100                 105                 110

Cys Ser Cys Thr Pro Gly Phe Ser Gly Lys Asp Cys Gln His Lys Ala
        115                 120                 125

Gly Pro Cys Val Ile Asn Gly Ser Pro Cys Gln His Gly Gly Ala Cys
    130                 135                 140

Val Asp Asp Glu Gly Gln Ala Ser His Ala Ser Cys Leu Cys Pro Pro
145                 150                 155                 160

Gly Phe Ser Gly Asn Phe Cys Glu Ile Val Ala Ala Thr Asn Ser Cys
                165                 170                 175

Thr Pro Asn Pro Cys Glu Asn Asp Gly Val Cys Thr Asp Ile Gly Gly
            180                 185                 190

Asp Phe Arg Cys Arg Cys Pro Ala Gly Phe Val Asp Lys Thr Cys Ser
        195                 200                 205

Arg Pro Val Ser Asn Cys Ala Ser Gly Pro Cys Gln Asn Gly Gly Thr
    210                 215                 220

Cys Leu Gln His Thr Gln Val Ser Phe Glu Cys Leu Cys Lys Pro Pro
225                 230                 235                 240

Phe Met Gly Pro Thr Cys Ala Lys Lys Arg Gly Ala Ser Pro Val Gln
                245                 250                 255

Val Thr His Leu Pro Ser Gly Tyr Gly Leu Thr Tyr Arg Leu Thr Pro
            260                 265                 270
```

```
Gly Val His Glu Leu Pro Val Gln Gln Pro Glu Gln His Ile Leu Lys
            275                 280                 285
Val Ser Met Lys Glu Leu Asn Lys Ser Thr Pro Leu Leu Thr Glu Gly
            290                 295                 300
Gln Ala Ile Cys Phe Thr Ile Leu Gly Val Leu Thr Ser Leu Val Val
305                 310                 315                 320
Leu Gly Thr Val Ala Ile Val Phe Leu Asn Lys Cys Glu Thr Trp Val
                325                 330                 335
Ser Asn Leu Arg Tyr Asn His Thr Phe Arg Lys Lys Asn Leu Leu
            340                 345                 350
Leu Gln Tyr Asn Ser Gly Glu Glu Leu Ala Val Asn Ile Ile Phe Pro
            355                 360                 365
Glu Lys Ile Asp Met Thr Thr Phe Asn Lys Glu Ala Gly Asp Glu Glu
            370                 375                 380
Ile
385

<210> SEQ ID NO 13
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane
      of hepatoblast

<400> SEQUENCE: 13

Tyr Glu Cys Ser Cys Ala Pro Gly Tyr Ser Gly Lys Asp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 14

Pro Cys Gly His Gly Gly Thr Cys Val Asp Asp Glu Gly
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 15

Cys Ala Asn Asn Gly Thr Cys Val Ser Leu Asp Gly Leu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast
```

-continued

```
<400> SEQUENCE: 16

Arg Ala Ser His Ala Ser Cys Leu Cys Pro Pro Gly Phe
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 17

Leu Cys Asp Arg Asp Val Arg Ala Cys Ser Ser Ala Pro
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 18

Ser Gly Asn Phe Cys Glu Ile Val Ala Asn Ser Cys Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 19

Pro Gly Gly Cys Ile Cys Thr Asp Gly Trp Asp Gly Glu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 21

Pro Asn Pro Cys Glu Asn Asp Gly Val Cys Thr Asp Ile
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Designed peptide based on amino acid sequences
      of extracellular domains in proteins expressed on cytomembrane of
      hepatoblast

<400> SEQUENCE: 21

Val Thr Ser Pro Gly Cys Leu His Gly Leu Cys Gly Glu
1               5                   10
```

```
<210> SEQ ID NO 22
<211> LENGTH: 13
<212> TYPE: PRT
<213> ORGANISM: Artificial Sequence
<220> FEATURE:
<223> OTHER INFORMATION: Control peptide

<400> SEQUENCE: 22

Asn Gln Val Ser Ile Gly Cys Pro Cys Asp Gly Lys Lys
1               5                   10
```